United States Patent
Rapp et al.

(10) Patent No.: US 12,336,785 B2
(45) Date of Patent: Jun. 24, 2025

(54) SYSTEMS AND METHODS FOR SURFACE PROFILE ESTIMATION VIA OPTICAL COHERENCE TOMOGRAPHY

(71) Applicant: Mitsubishi Electric Research Laboratories, Inc., Cambridge, MA (US)

(72) Inventors: Joshua Rapp, Somerville, MA (US); Hassan Mansour, Boston, AL (US); Petros Boufounos, Winchester, AL (US); Philip Orlik, Cambridge, MA (US); Toshiaki Koike Akino, Cambridge, AL (US); Kieran Parsons, Cambridge, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 211 days.

(21) Appl. No.: 17/932,215

(22) Filed: Sep. 14, 2022

(65) Prior Publication Data

US 2024/0090768 A1  Mar. 21, 2024

(51) Int. Cl.
*A61B 5/00* (2006.01)
*G01B 9/02* (2022.01)
(Continued)

(52) U.S. Cl.
CPC ........ *A61B 5/0066* (2013.01); *G01B 9/02088* (2013.01); *G01B 9/0209* (2013.01); *G01B 9/02091* (2013.01); *G01B 9/02044* (2013.01)

(58) Field of Classification Search
CPC ............. A61B 5/0066; G01B 9/02088; G01B 9/0209; G01B 9/02091; G01B 9/02044
(Continued)

(56) References Cited

U.S. PATENT DOCUMENTS 6,002,480 A * 12/1999 Izatt .................. G01B 9/02072
                                                          356/479
6,377,349 B1 * 4/2002 Fercher ..................... G01J 9/02
                                                          356/497
(Continued)

FOREIGN PATENT DOCUMENTS

WO   WO-2014193310 A1 * 12/2014 ............. A61B 3/102

OTHER PUBLICATIONS

Takashi Endo, Yoshiaki Yasuno, Shuichi Makita, Masahide Itoh, and Toyohiko Yatagai, "Profilometry with line-field Fourier-domain interferometry," Opt. Express 13, 695-701 (2005) (Year: 2005).*
(Continued)

*Primary Examiner* — Michelle M Iacoletti
*Assistant Examiner* — Noah J. Haney
(74) *Attorney, Agent, or Firm* — Gene Vinokur

(57) ABSTRACT

An optical coherence tomography (OCT) system comprises an interferometer configured to split incident light into a reference beam and a test beam, and to interfere the test beam reflected from the specimen with the reference beam reflected from a reference mirror to produce an interference pattern. The OCT system also comprises a spectrometer configured to analyze spectral components of the interference pattern at non-uniformly sampled wavenumbers. A computer-readable memory of the OCT system is configured to store a measurement model with elements connecting different depth values with different non-uniformly sampled wavenumbers and weighted with weights derived from a power spectral density (PSD) of the incident light for corresponding wavenumbers. The OCT system further comprises a processor configured to determine the profilometry measurements of the specimen as a maximum likelihood estimate of the specimen surface depth by back-projection of the measured intensities with the measurement model.

20 Claims, 17 Drawing Sheets

(51) Int. Cl.
 *G01B 9/0209* (2022.01)
 *G01B 9/02091* (2022.01)
(58) Field of Classification Search
 USPC .......................................................... 356/477
 See application file for complete search history.

(56) References Cited

U.S. PATENT DOCUMENTS

| | | | | |
|---|---|---|---|---|
| 7,978,346 | B1* | 7/2011 | Riza | G02B 21/0072 |
| | | | | 356/627 |
| 9,347,765 | B2 | 5/2016 | Kemp et al. | |
| 2009/0185191 | A1* | 7/2009 | Boppart | A61B 5/6852 |
| | | | | 356/479 |
| 2010/0027019 | A1* | 2/2010 | Suehira | G01B 9/02091 |
| | | | | 356/450 |
| 2016/0213253 | A1* | 7/2016 | Wang | A61B 5/14556 |

OTHER PUBLICATIONS

Jinxin Huang, Eric Clarkson, Matthew Kupinski, Kye-sung Lee, Kara L. Maki, David S. Ross, James V. Aquavella, and Jannick P. Rolland, "Maximum-likelihood estimation in Optical Coherence Tomography in the context of the tear film dynamics," Biomed. Opt. Express 4, 1806-1816 (2013) (Year: 2013).*

T. Endo, Y. Yasuno, S. Makita, M. Itoh, and T. Yatagai, "Profilometry with line-field Fourier-domain interferometry," Opt. Express, OE, vol. 13, No. 3, pp. 695-701, Feb. 2005, doi: 10.1364/OPEX.13.000695.

S. Lawman and H. Liang, "High precision dynamic multi-interface profilometry with optical coherence tomography," Appl. Opt., AO, vol. 50, No. 32, pp. 6039-6048, Nov. 2011, doi: 10.1364/AO.50.006039.

N. J. Suliali, P. Baricholo, P. H. Neethling, and E. G. Rohwer, "Development of a low-cost, 11 μm spectral domain optical coherence tomography surface profilometry prototype," in Optical Measurement Systems for Industrial Inspection X, Jun. 2017, vol. 10329, pp. 666-673. doi: 10.1117/12.2268064.

* cited by examiner

SYSTEMS AND METHODS FOR SURFACE PROFILE ESTIMATION VIA OPTICAL COHERENCE TOMOGRAPHY

TECHNICAL FIELD

The present disclosure relates generally to imaging and more particularly to an optical coherence tomography (OCT) system and method for producing profilometry measurements of a specimen.

BACKGROUND

Profilometry is a technique used to extract topographical data from a surface. This can be a single point, a line scan or even a full three-dimensional scan. The purpose of profilometry is to get surface morphology, step heights and surface roughness. In many applications, electromagnetic sensing is used for profilometry measurements to obtain information about the surface or subsurface of a particular specimen. One such technique is tomography. Tomography can be used for various applications, for example, radiology, biology, materials science, manufacturing, quality assurance, quality control, or the like. Some types of tomography include, for example, optical coherence tomography (OCT), x-ray tomography, positron emission tomography, optical projection tomography, and the like.

OCT is a technology used to perform high-resolution cross-sectional imaging. It is often applied to imaging biological tissue structures, such as the human eye, for example, on microscopic scales in real time. Optical waves are reflected from an object or sample and a computer produces images of cross sections or three-dimensional volume renderings of the sample by using information on how the waves are changed upon reflection.

OCT is an interferometric imaging technique that coherently mixes an optical signal from the target with a reference signal. OCT offers non-invasive, noncontact label-free imaging of the specimen with micron-scale resolution in three dimensions. Due to the ability of OCT to achieve micron-scale resolution, it is used across various technical disciplines including factory automation process checking the integrity of assembly or manufacturing operations, as well as in various medical specialties including ophthalmology and cardiology.

OCT may be performed based on time-domain processing (time-domain OCT or TD-OCT) or Fourier-domain processing (Fourier-domain OCT or FD-OCT). In time domain OCT (TD-OCT), the path length difference between light returning from the sample and reference light is translated longitudinally in time to recover the depth information in the sample. In frequency-domain or Fourier-domain OCT (FD-OCT), the broadband interference between reflected sample light and reference light is acquired in the frequency domain and a Fourier transform is used to recover the depth information.

The sensitivity advantage of FD-OCT over TD-OCT is well established. However, the FD-OCT still suffers from measurement noise and may require extra computational and subsampling methods to improve the accuracy of profilometry estimations. See, e.g., U.S. Pat. No. 10,502,544.

SUMMARY

It is an object of some embodiments to provide an optical coherence tomography (OCT) system and method for producing profilometry measurements of a specimen. Additionally, or alternatively, it is an object of some embodiments to provide a system and a method for Fourier-domain OCT (FD-OCT) with an improved signal-to-noise ratio (SNR) of recovered depth information. Additionally, or alternatively, it is an object of some embodiments to overcome the above-mentioned drawbacks of the FD-OCT methods.

The OCT uses the interference of two beams of light to measure differences in path length. The beat frequency of the interfered light is much lower than the oscillation frequency of light, allowing OCT to achieve fine depth resolution without high-bandwidth electronics. The FD-OCT profilometry takes advantage of the fast Fourier transform (FFT)-based processing over values of wavenumbers of the interfered signal. Applying the Fourier transform to the interfered signal uniformly sampled in wavenumber should yield a sharp peak in the depth domain. However, OCT systems typically sample the interfered light with uniform wavelength $\lambda$, which means the samples are non-uniformly spaced in wavenumber $k=2\pi/\lambda$. The processor in an FD-OCT system can interpolate the data and resample uniformly in wavenumber k, so that the inverse fast Fourier transform (IFFT) can be used to process the measurements. However, the interpolation process also propagates the noise to the unsampled wavenumbers, which reduces the robustness to noise, especially for higher frequency interference patterns that correspond to the deepest features of the sample.

Some embodiments are based on a recognition that instead of using the FFT to recover the depth for a single reflector, the depth can be recovered from the back-projection of the measurements. Back-projection reverses the mapping from the depth domain to the measurement domain via a model of the measurement system. Because back-projection is usually not equivalent to inverting this mapping, it is not suitable for recovering the depths of multiple reflectors. As such, the FFT with interpolated wavenumbers is usually advantageous over back-projection because it computes an approximate inverse. Hence, it should not come as a surprise that to the best of available knowledge, the back-projection is not used for the profilometry measurements. However, some embodiments are based on the realization that under certain conditions the back-projection can be adapted to outperform the FFT.

Various embodiments adapt the back-projection by modifying a measurement matrix as well as the structure of the recovered data. Specifically, in some embodiments, the back-projection f=M*y produces a vector f from measurements y using a measurement matrix M. For opaque surface measurement, the largest element of vector f can be determined as the approximate maximum likelihood estimate for a single surface depth, avoiding an interpolation of the inputs of the back-projection.

In addition, some embodiments are based on an understanding of the nature of the profilometric measurements using an interferometer. The interferometer produces an interference pattern of a beat signal that is analyzed to measure intensities of uniformly sampled wavelengths in the interference pattern. This uniform sampling of the wavelength is due to the nature of the physics of diffraction. However, there is a nonlinear relationship between wavenumber and wavelength $k_n=2\pi/\lambda_n$, such that the intensities of the uniformly sampled wavelengths correspond to non-uniformly sampled wavenumbers.

In contrast with FFT requiring the uniformly sampled wavenumbers, the measurement matrix can be defined directly for the non-uniformly sampled wavenumbers corresponding to the uniformly sampled wavelengths of the interference pattern. Moreover, for a depth range of interest, it is possible to determine such a measurement model that has elements connecting different depth values with different non-uniformly sampled wavenumbers corresponding to the uniformly sampled wavelength. In such a manner, the interpolation inside the back-projection can also be avoided.

In addition, in contrast with the FFT, the measurement matrix of some embodiments includes not only the depths and the wavenumbers but also the power spectral density (PSD) $S(k_n)$ determined for different wavenumbers $k_n$. This is equivalent to an amplitude envelope that multiplies the measurements.

The PSD in the measurement matrix accounts for the weight each element of the data should receive in back-projection. In such a manner, the PSD increases the robustness of back-projection by relying more heavily on samples with higher envelope amplitude.

Additionally, some embodiments define measurement matrix M explicitly for a set of possible depths $z_m$ for m=0, ..., M−1. These possible depths may be chosen at any coarse or fine resolution as desired and over whatever range of depths is relevant. For instance, OCT measurements typically measure with respect to a reference depth z=0. The sample is kept entirely above or below the reference depth, otherwise, an ambiguity occurs. Therefore, it is possible to reconstruct only positive (or only negative) depth values.

Some example embodiments may be realized for process monitoring in manufacturing. For example, without limitation, some example embodiments may be included in computer numerical control (CNC) machines, such as mills, electric discharge machines (EDMs), wire EDMs, etc.

In order to achieve the aforementioned objectives and advantages, some example embodiments provide systems, methods, and programs for profilometry measurements of a specimen.

For example, some example embodiments provide an OCT system for profilometry measurements of a specimen. The OCT system comprises an interferometer configured to split incident light into a reference beam and a test beam, and to interfere the test beam reflected from the specimen with the reference beam reflected from a reference mirror to produce an interference pattern. The OCT system also comprises a spectrometer configured to analyze spectral components of the interference pattern at non-uniformly sampled wavenumbers. A computer-readable memory of the OCT system is configured to store a measurement model with elements connecting different depth values with different non-uniformly sampled wavenumbers and weighted with weights derived from a power spectral density (PSD) of the incident light for corresponding wavenumbers. The OCT system further comprises a processor configured to determine the profilometry measurements of the specimen as a maximum likelihood estimate of the specimen surface depth by back-projection of the measured intensities with the measurement model.

Some example embodiments also provide a method for profilometry measurements of a specimen in an OCT system. The method comprises splitting by an interferometer, incident light into a reference beam and a test beam, and interfering the test beam reflected from the specimen with the reference beam reflected from a reference mirror to produce an interference pattern. The method further comprises analyzing by a spectrometer, spectral components of the interference pattern at non-uniformly sampled wavenumbers. A computer-readable memory of the OCT system stores a measurement model with elements connecting different depth values with different non-uniformly sampled wavenumbers and weighted with weights derived from a power spectral density (PSD) of the incident light for corresponding wavenumbers. The method further comprises determining the profilometry measurements of the specimen as a maximum likelihood estimate of the specimen surface depth by back-projection of the measured intensities with the measurement model.

Some example embodiments also provide a non-transitory computer readable medium having stored thereon computer executable instructions which when executed by a computer, cause the computer to perform a method for profilometry measurements of a specimen in an OCT system. The method comprises splitting by an interferometer, incident light into a reference beam and a test beam, and interfering the test beam reflected from the specimen with the reference beam reflected from a reference mirror to produce an interference pattern. The method further comprises analyzing by a spectrometer, spectral components of the interference pattern at non-uniformly sampled wavenumbers. A computer-readable memory of the OCT system stores a measurement model with elements connecting different depth values with different non-uniformly sampled wavenumbers and weighted with weights derived from a power spectral density (PSD) of the incident light for corresponding wavenumbers. The method further comprises determining the profilometry measurements of the specimen as a maximum likelihood estimate of the specimen surface depth by back-projection of the measured intensities with the measurement model.

According to some example embodiments, the depth values are uniformly sampled from a depth-measurement range with a resolution of the OCT system. The depth values may be relative values with respect to a reference depth selected outside of the depth-measurement range.

As a part of the method, each profilometry measurement may be estimated by executing a maximum likelihood estimator (MLE) to produce an argument of the maximum likelihood estimate of the non-zero element in the reflectivity vector corresponding. Further, each argument of the reflectivity vector corresponds to one of the depth values in the measurement model. Furthermore, the MLE may be an approximate MLE, and the execution of the approximate MLE comprises backprojecting the data vector through the measurement matrix. The MLE may be the depth value corresponding to the largest-magnitude element in the back-projection.

According to some example embodiments, the MLE may be an exact MLE, and the execution of the exact MLE comprises refining the approximate MLE by maximizing the maximum likelihood objective function using a gradient-free optimization method.

BRIEF DESCRIPTION OF THE DRAWINGS

The presently disclosed embodiments will be further explained with reference to the following drawings. The drawings shown are not necessarily to scale, with emphasis instead generally being placed upon illustrating the principles of the presently disclosed embodiments.

Figure 1A:
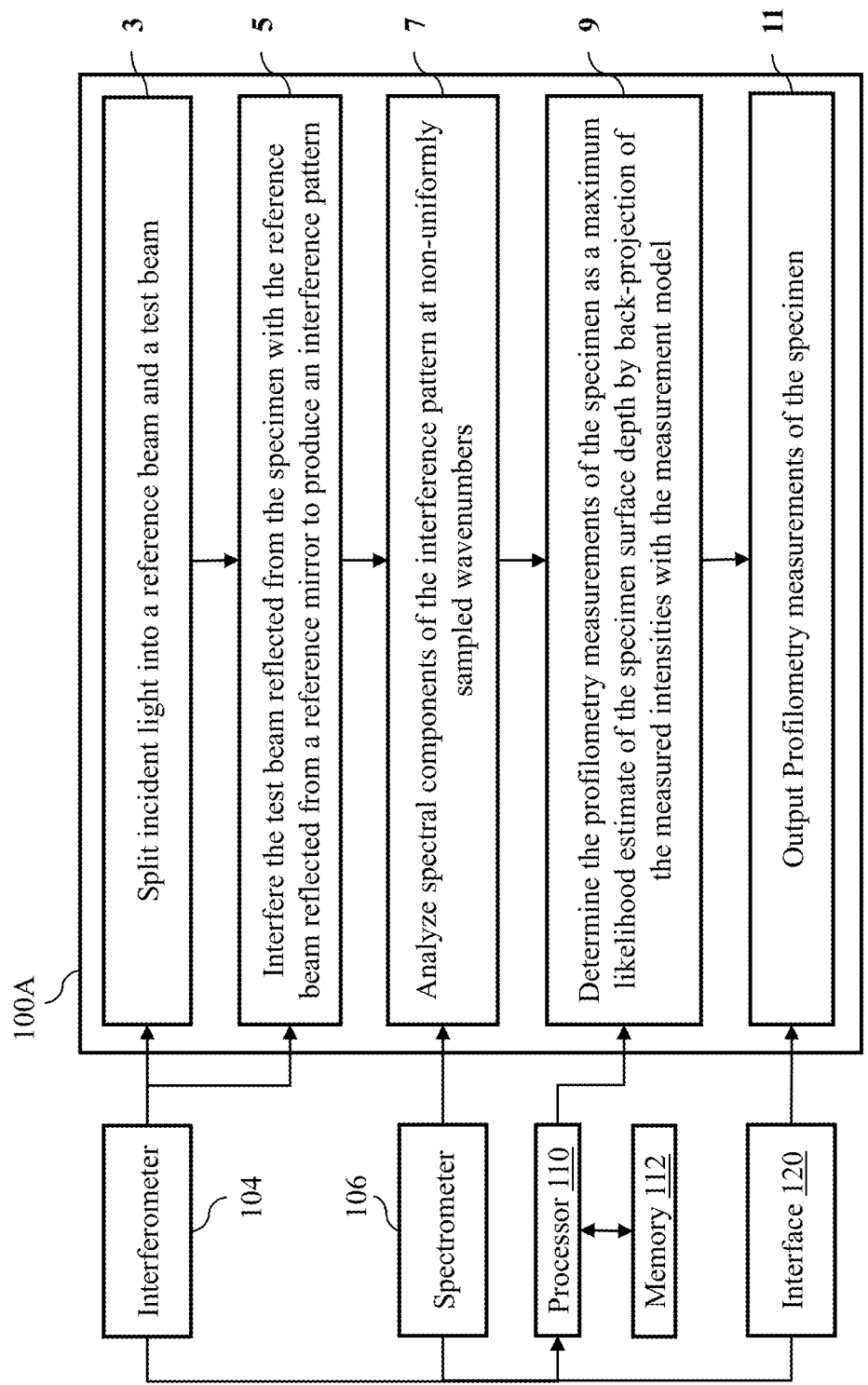
FIG. 1A illustrates a method 100A for profilometry measurements of a specimen in an Optical Coherence Tomography (OCT) system, according to some example embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. Contemplated are various changes that may be made in the function and arrangement of elements without departing from the spirit and scope of the subject matter disclosed as set forth in the appended claims.

Specific details are given in the following description to provide a thorough understanding of the embodiments. However, understood by one of ordinary skill in the art can be that the embodiments may be practiced without these specific details. For example, systems, processes, and other elements in the subject matter disclosed may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicate like elements.

Also, individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but may have additional steps not discussed or included in a figure. Furthermore, not all operations in any particularly described process may occur in all embodiments. A process may correspond to a method, a function, a procedure, a subroutine, a subprogram, etc. When a process corresponds to a function, the function's termination can correspond to a return of the function to the calling function or the main function.

Furthermore, embodiments of the subject matter disclosed may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine-readable medium. A processor(s) may perform the necessary tasks.

In order to measure the surface profile of a material surface, a quantified measurement of the material surface is required. This can be done by profilometry, in which a probe, mechanical (contact) or optical (noncontact), is passed across the surface. The probe follows the contours at each point on the surface, and the height of the probe at each point is recorded and the resulting 1D scan or a 2D map is analyzed. Parameters such as arithmetic average of the absolute values of all points of the profile (Ra), root means square values of all the heights around the mean (Rq) are often used to quantify the roughness. Profilometers generate an image of the surface height. Size of the area measured and the size of the probe set the upper and lower limits on the size of the features that can be characterized. The nature of the probe limits the range of surfaces that can be investigated by these techniques. In this regard optical techniques are more appropriate for relatively soft materials.

Optical profilometry is a more recent and modern approach and has been developed to increase accuracy. Briefly, a source of light is used to scan the sample surface and the light beam diffracted by the surface roughness is collected on a mirror. The image generated is the deviation of the light beam on the mirror. With this technique, it is possible theoretically to assess the roughness as low as a nanometer.

Optical profilometry is a rapid, nondestructive, and non-contact surface metrology technique. An optical profiler is a type of microscope in which light from a lamp is split into two paths by a beam splitter. One path directs the light onto the surface under test, the other path directs the light to a reference mirror. Reflections from the two surfaces are recombined and projected onto an array detector. When the path difference between the recombined beams is on the order of a few wavelengths of light or less interference can occur. This interference contains information about the surface contours of the test surface. Vertical resolution can be on the order of several angstroms while lateral resolution depends upon the objective and is typically in the range of few microns.

In many applications, electromagnetic sensing is used for profilometry measurements to obtain information about the surface or subsurface of a particular specimen. One such technique is tomography. Some types of tomography include, for example, optical coherence tomography (OCT), x-ray tomography, positron emission tomography, optical projection tomography, and the like. OCT is a technology used to perform high-resolution cross-sectional imaging. It is often applied to imaging biological tissue structures, such as the human eye, for example, on microscopic scales in real time. Optical waves are reflected from an object or sample and a computer produces images of cross sections or three-dimensional volume renderings of the sample by using information on how the waves are changed upon reflection.

The OCT uses the interference of two beams of light to measure differences in path length. The beat frequency of the interfered light is much lower than the oscillation frequency of light which reduces the need for high-bandwidth electronics. The FD-OCT profilometry takes advantage of the fast Fourier transform (FFT)-based processing over values of wavenumbers of the interfered signal. Applying the Fourier transform to the interfered signal uniformly sampled in wavenumber should yield a sharp peak in the depth domain. However, OCT systems typically sample the interfered light with uniform wavelength $\lambda$, which means the samples are non-uniformly spaced in wavenumber $k=2\pi/\lambda$. The processor in an FD-OCT system can interpolate the data and resample uniformly in wavenumber k, so that the inverse fast Fourier transform (IFFT) can be used to process the measurements. However, the interpolation process also propagates the noise to the unsampled wavenumbers, which reduces the robustness to noise, especially for higher frequency interference patterns that correspond to the deepest features of the sample.

FIG. 1A illustrates a method 100A for profilometry measurements of a specimen in an OCT system, according to some example embodiments. The method 100A may be executed by some or all components of an OCT system which is described later in detail with reference to FIG. 1B. The profilometry measurement method 100A comprises splitting 3 an incident light beam into a reference beam and a test beam. This may be performed by an interferometer 104 of the OCT system. According to some example embodiments, in this regard a beamsplitter may be utilized. At step 5, the method 100A comprises interfering the test beam reflected from the specimen with the reference beam reflected from a reference mirror to produce an interference pattern.

At step 7, the method comprises analyzing spectral components of the interference pattern at non-uniformly sampled wavenumbers. At step 9, the processor 110 of the OCT system utilizes a computer readable memory 112 and determines the profilometry measurements of the specimen as a maximum likelihood estimate of the specimen surface depth by back-projection of the measured intensities with the measurement model. The computer-readable memory 112 of the OCT system is configured to store a measurement model with elements connecting different depth values with different non-uniformly sampled wavenumbers and weighted with weights derived from a power spectral density (PSD) of the incident light for corresponding wavenumbers.

According to some example embodiments, the depth values are uniformly sampled from a depth-measurement range with a resolution of the OCT system. In some example embodiments, the depth values are relative values with respect to a reference depth selected outside of the depth-measurement range. The profilometry measurements thus determined by the processor 110 may be output 11 via an interface 120 of the OCT system.

One or more components such as the interferometer 104, the spectrometer 106, the interface 120 and/or the memory 112 may be communicatively coupled to the processor 110. The processor 110 may additionally be coupled to one or more additional processing circuitry to perform additional processing. The processor 110 may perform one or more operations such as communicate, read/write and/or control operations of the above mentioned one or more components. The profilometry measurement method comprises several modules which will be explained hereinafter in detail. Firstly, an overview of the OCT system is provided with reference to FIGS. 1B and 1C to understand the components and elements utilized to realize the OCT system.

Figure 1B:
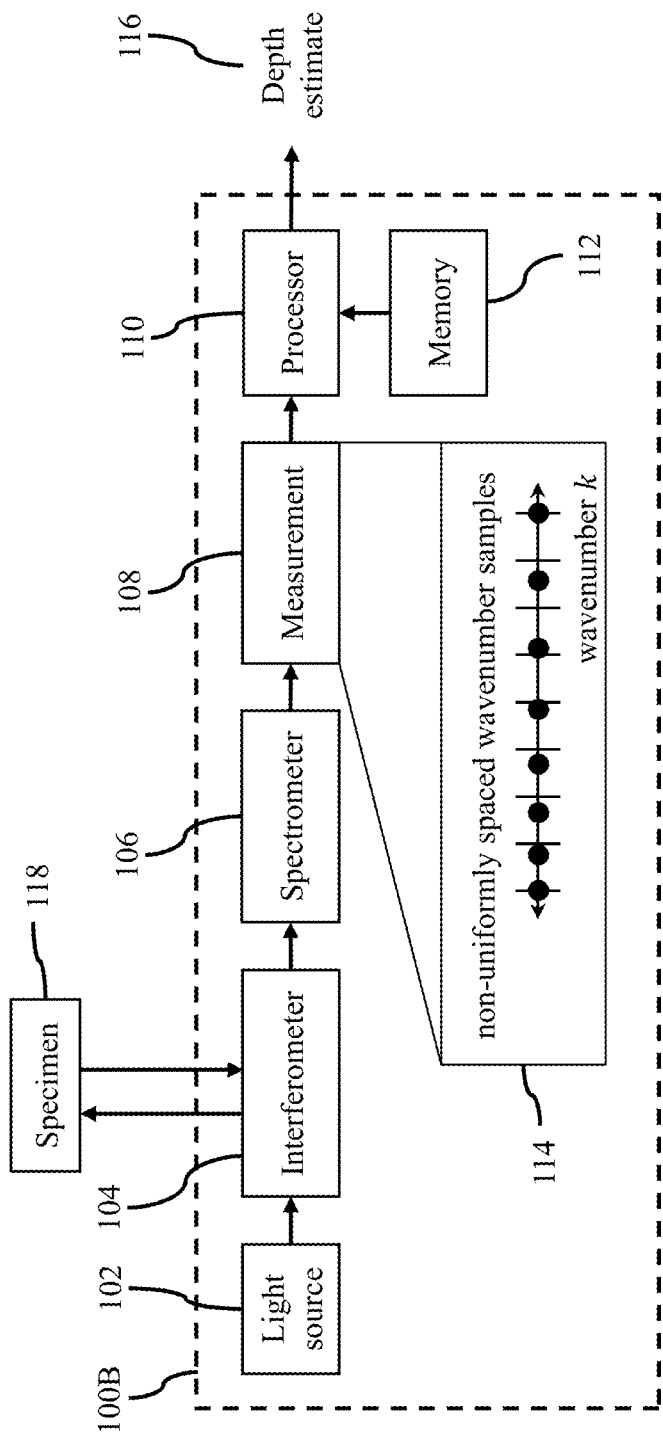
FIG. 1B shows a schematic of an OCT system for producing profilometry measurements of a specimen from measurements non-uniformly sampled in wavenumber, according to some example embodiments.

FIG. 1B illustrates a schematic of an OCT system 100B that produces a depth estimate 116 of a specimen 118 from a measurement 108 made at non-uniformly sampled wavenumbers 114. The OCT system 100B comprises a light source 102 (also referred to as illumination source), an interferometer 104, a spectrometer 106, a processor 110, and memory 112. In some example embodiments, the specimen 118 may be opaque and may have a single visible surface.

The light source 102 may comprise any suitable illumination source that provides a light beam or an electromagnetic beam for investigating a specimen. The choice of the illumination source may be dependent on the subject specimen and/or the intended application of the OCT system. For example, without limitation the light source 102 may comprise one or more of a tunable LASER, an LED array, an incandescent source, a noble gas-based lamp, a radiation source such as an X-ray generator, a photon emitter, a positron emitter or the like. According to some example embodiments, the light source 102 includes one or a combination of a laser, a superluminescent diode (SLD), or a light-emitting diode (LED).

In some example embodiments, the light source 102 may be configured to utilize planar geometry, fan-beam geometry, pointwise illumination, or any combination thereof. Pointwise illumination may be provided by any beam steering mirror-like devices such as electromechanical, optoelectronic, acousto-optic, all optical-based technology, liquid-crystal-based mirror, and any other such devices.

A beam originating from the light source 102 may comprise light with coaxial, orthogonal polarizations and/or with different optical frequencies. The beam is split by a beam splitter of an interferometer 104. In some example embodiments, the interferometer 104 may be a Michelson interferometer. In some example embodiments, the interferometer 104 may be a Linnik interferometer. According to some example embodiments, the beam splitter may be a partially reflecting mirror. In some example embodiments, the beam splitter may be a non-polarizing beam splitter. The beam splitter may split the beam into a reference illumination that is transmitted to the reference mirror and a sample illumination that is transmitted to a specimen 118.

According to some example embodiments, the beam splitter may comprise a series of beam splitters and/or polarizers if required. The sample illumination is incident on the specimen 118 and all or a portion of the sample illumination may be reflected from the specimen towards the beam splitter. The reflected signal from the specimen 118 may be split by the beam splitter and at least a part thereof gets combined with the reflected reference illumination and directed towards the detector array of the spectrometer 106 for further analysis and detection. The detector array of the spectrometer 106 may comprise suitable imaging devices such as a charge coupled device camera. The detector array may provide one or more detection signals corresponding to a recombination of the reflected signal and the reference signal.

The sample illumination may include an electromagnetic two-dimensional (2D) field directed by the interferometer 104 to form an axial scan of the specimen 118, such that the measured intensities of interference pattern include measurements corresponding to a sequence of points on a line of the specimen 118. In some example embodiments, the OCT system 100B may also include one or more actuators for directing the incident light into another line parallel to a line of a previous scan.

The processor 110 may extract a sequence of intensities corresponding to the sequence of points on the line of the specimen 118. Additionally, the processor 110 may process the intensities of different points concurrently with each, to produce the profilometry measurements for the sequence of points. In some example embodiments, the OCT system 100B may comprise or be additionally coupled to one or more processing circuitry for producing in parallel, the profilometry measurements for at least some points in the sequence of points. The one or more processing circuitry may comprise suitable processing means such as processors and memories.

According to some example embodiments, the OCT system 100B may additionally comprise a line-field generator including an extended light source of an angular size greater than a lateral resolution across the profilometry measurements, a lens arranged on a path of light emitted by the extended light source for focusing the light into an extended line-field light of a width greater than the lateral resolution, and a filter arranged in a focal plane of the lens for spatially filtering the extended line-field light into the incident light with a line-field of a width equal to the lateral resolution.

Figure 1C:
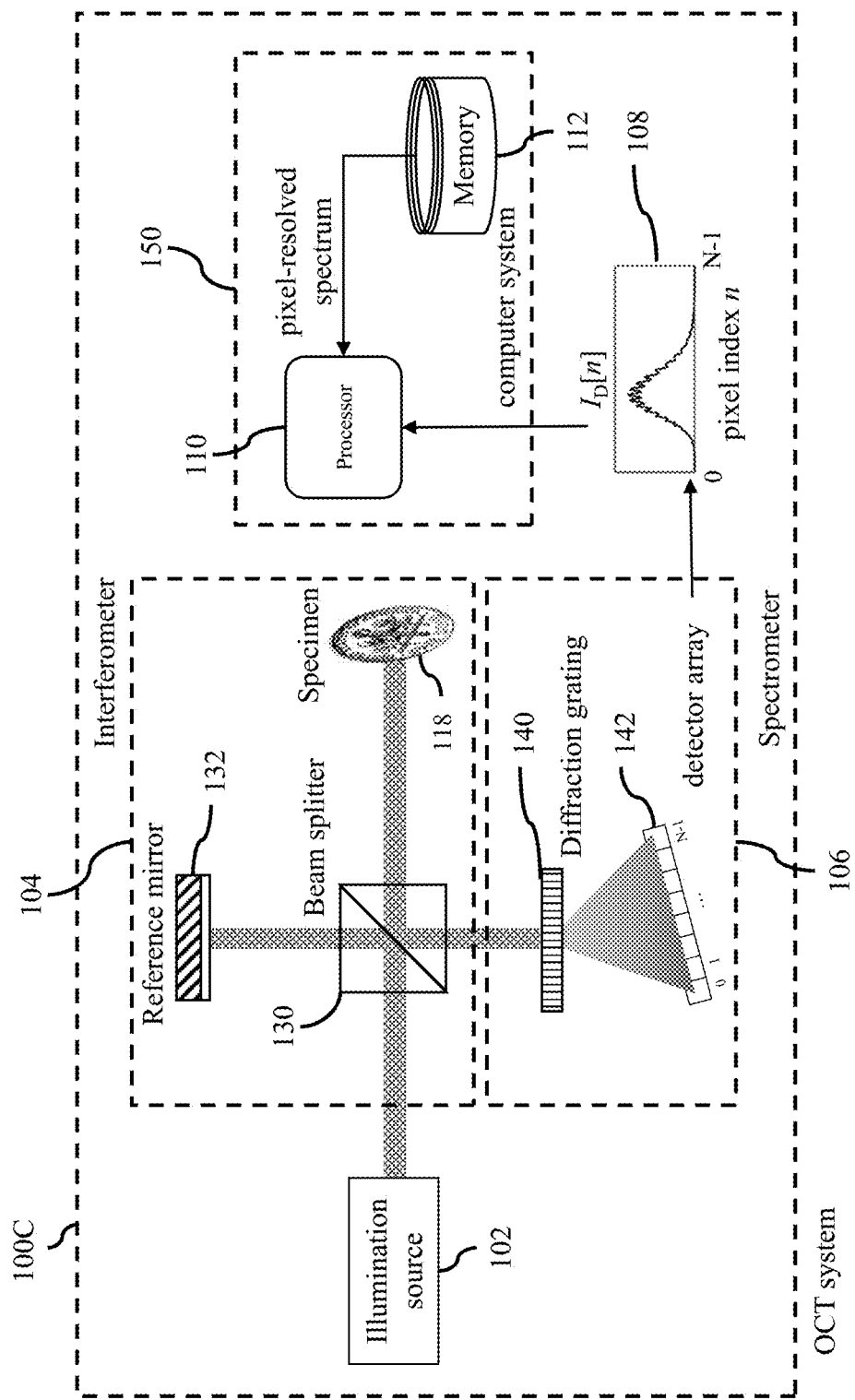
FIG. 1C shows a detailed schematic of the OCT system for producing profilometry measurements of a specimen, according to some example embodiments.

FIG. 1C illustrates a detailed schematic of an OCT system 100C, according to some example embodiments. Illumination source 102 may be a broadband source and may emit a polychromatic plane wave, whose electric field is given as $E_I = s(k, \omega) \exp[i(kz-\omega t)]$, with wavenumber $k=2\pi/\lambda$, wavelength $\lambda$, temporal frequency $\omega$, and amplitude spectrum $s(k, \omega)$. The 50/50 beamsplitter 130 splits the incident light into the two arms of the interferometer 104. After reflecting from the reference mirror 132, the field entering the beamsplitter from the reference arm is $$E_R = \frac{s(k, \omega)}{\sqrt{2}} r_R \exp[i(2kz_R - \omega t)],$$

which accounts for the $2z_R$ roundtrip path length in the reference arm, the reference reflectivity $r_R$, and the beamsplitter decreasing the intensity by half. In the sample arm, the electric field is a convolution of the incident light with the depth-dependent sample reflectivity profile. Although in OCT the reflectivity profile is generally continuous or described as a series of discrete reflectors, for an opaque specimen 118 with a single reflector at depth $z_S$ with reflectivity $r_S$, the electric field is $$E_S = \frac{s(k, \omega)}{\sqrt{2}} r_S \exp[i(2kz_S - \omega t + \phi)],$$

where $\phi$ accounts for any phase shift incurred by reflection from the sample. The light reflects from the reference mirror 132 and the specimen 118 in the sample arm and is recombined by the beamsplitter 130, and the total intensity at the detector is $$I(k, \omega) = \frac{1}{2} \langle |E_R + E_S|^2 \rangle = \frac{1}{4} S(k) \{r_R^2 + r_S^2 + 2r_R r_S \cos[2k(z_S - z_R) + \phi]\},$$

where $S(k) = \langle |s(k, \omega)|^2 \rangle$ is the illumination source power spectral density (PSD) and the angle brackets $\langle \cdot \rangle$ denote temporal averaging. Note that $I(k, \omega)$ has only constant amplitude offset and interference terms—there is no "autocorrelation" term as typically found when multiple surfaces mutually interfere in OCT.

The spectrometer 106 has a diffraction grating 140 that separates the interference intensity by wavelength. The diffraction grating 140 diffracts different beams of different wavelengths forming the interference pattern into different diffraction angles. The intensity of the combined light is measured with array detector 142, with each detector pixel indexed $n=0, \ldots, N-1$ measuring a separate wavelength $\lambda_n$. The corresponding wavenumber is defined as $k_n = 2\pi/\lambda_n$, and the Power Spectral Density (PSD) at that wavenumber is $S(k_n)$. The detector measurement is the intensity scaled by the detector responsivity $\rho$.

For specimen 118 consisting of a single opaque reflector, the intensity measured at each pixel in detector array 142 is the measurement 108 given by $$I_D[n] = \frac{\rho}{4} S(k_n) \{r_R^2 + r_S^2 + 2r_R r_S \cos[2k_n(z_S - z_R) + \phi]\} + v[n],$$

where noise $v[n]$ is assumed to be zero-mean, white, and Gaussian.

The steps of preprocessing and depth estimation may be performed by the processor 110 of the computer system 150. The DC components are removed from measurement 108. In some example embodiments, the DC components are removed by subtracting the scaled PSD from the raw measurements as $$y[n] = \frac{2}{\rho r_R^2} \{I_D[n] - \frac{\rho}{4} S(k_n) r_R^2 (1 + a^2)\}.$$

In some example embodiments, the DC components are removed by applying a high-pass filter to the raw measurements. The resulting interference data vector y has a value for element n given as:

$$y_n = S(k_n) a \cos(2k_n z_D + \phi) + w[n],$$

where $a = r_S/r_R$ is the relative reflectivity, $z_D = z_S - z_R$ is the relative depth, and $w[n] = 2v[n]/\rho r_R^2$ is zero-mean, white Gaussian noise with variance $\sigma_w^2$.

As described above, the spectrometer 106 includes the diffraction grating 140 and a detector array 142. The detector array 142 may have detecting elements arranged at the different diffraction angles to measure intensities of different beams corresponding to the intensities of the uniformly sampled wavelengths in the interference pattern. The detecting elements of the detector array 142 are calibrated to map each index of the detecting elements in the detector array with a corresponding wavelength.

Figure 2A:
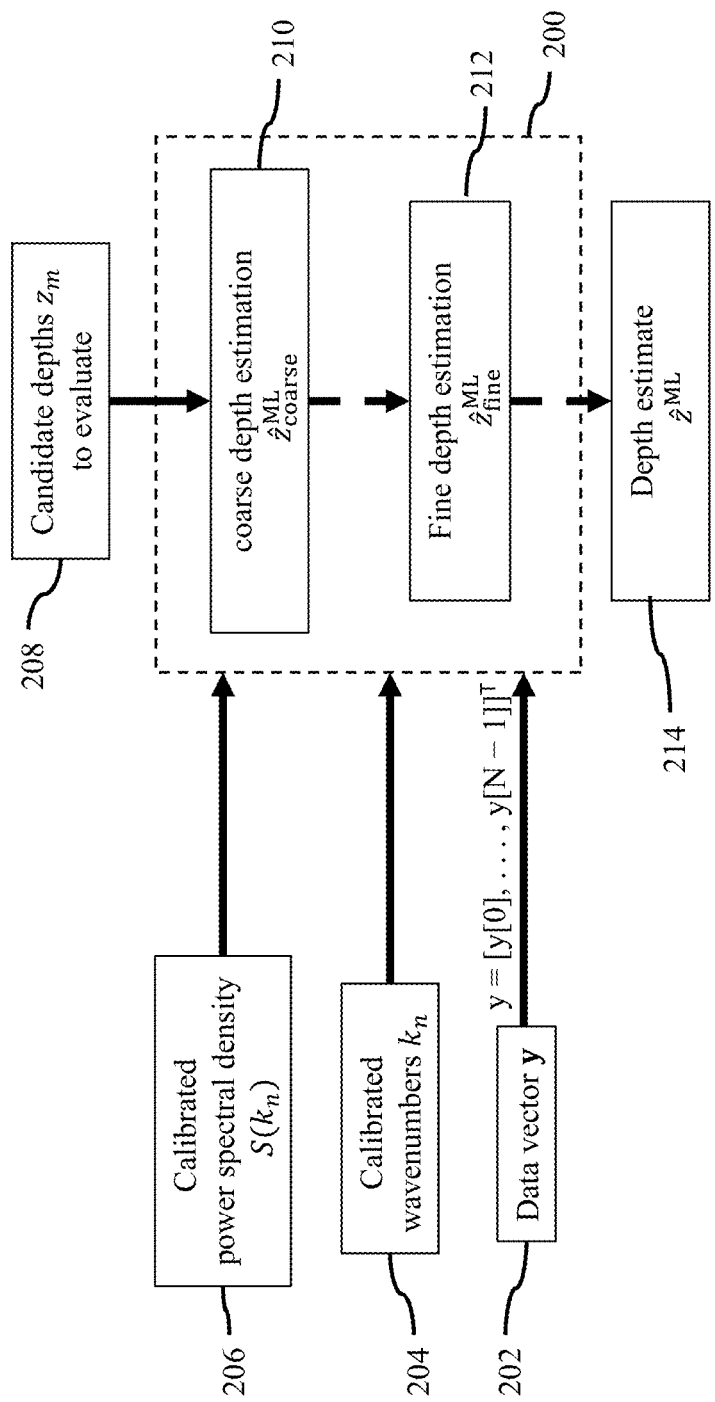
FIG. 2A illustrates the process of determining the maximum likelihood estimator (MLE) for the depth of the specimen surface, according to some example embodiments.

FIG. 2A depicts the process 200 of determining the maximum likelihood estimator (MLE) 214 for the depth of the specimen surface 118, given the data vector 202, wavenumber calibration 204, power spectral density calibration 206, and a set of candidate depths 208. Assuming the noise is Gaussian, the likelihood of observing data y is $$p(y; a, z, \phi) = \frac{1}{(2\pi\sigma_w^2)^{\frac{N}{2}}} \exp\left(-\frac{1}{2\sigma_w^2} \sum_{n=0}^{N-1} \{y[n] - S(k_n) a \cos(2k_n z + \phi)\}^2\right).$$

The maximum likelihood estimate depth is then the value of z that minimizes $$-\log p(y; a, z, \phi) = \sum_{n=0}^{N-1} \{y[n] - S(k_n) a \cos(2k_n z + \Phi)\}^2,$$

which ignores constant terms. Because the negative log-likelihood is highly multi-modal, it is advantageous to perform the minimization in a two-step procedure of coarse 210 and fine 212 estimation. In some example embodiments, the coarse estimation step 210 may be sufficient for the depth estimation 214 and in such case, the fine depth estimation step 212 may be optional.

Figure 2B:
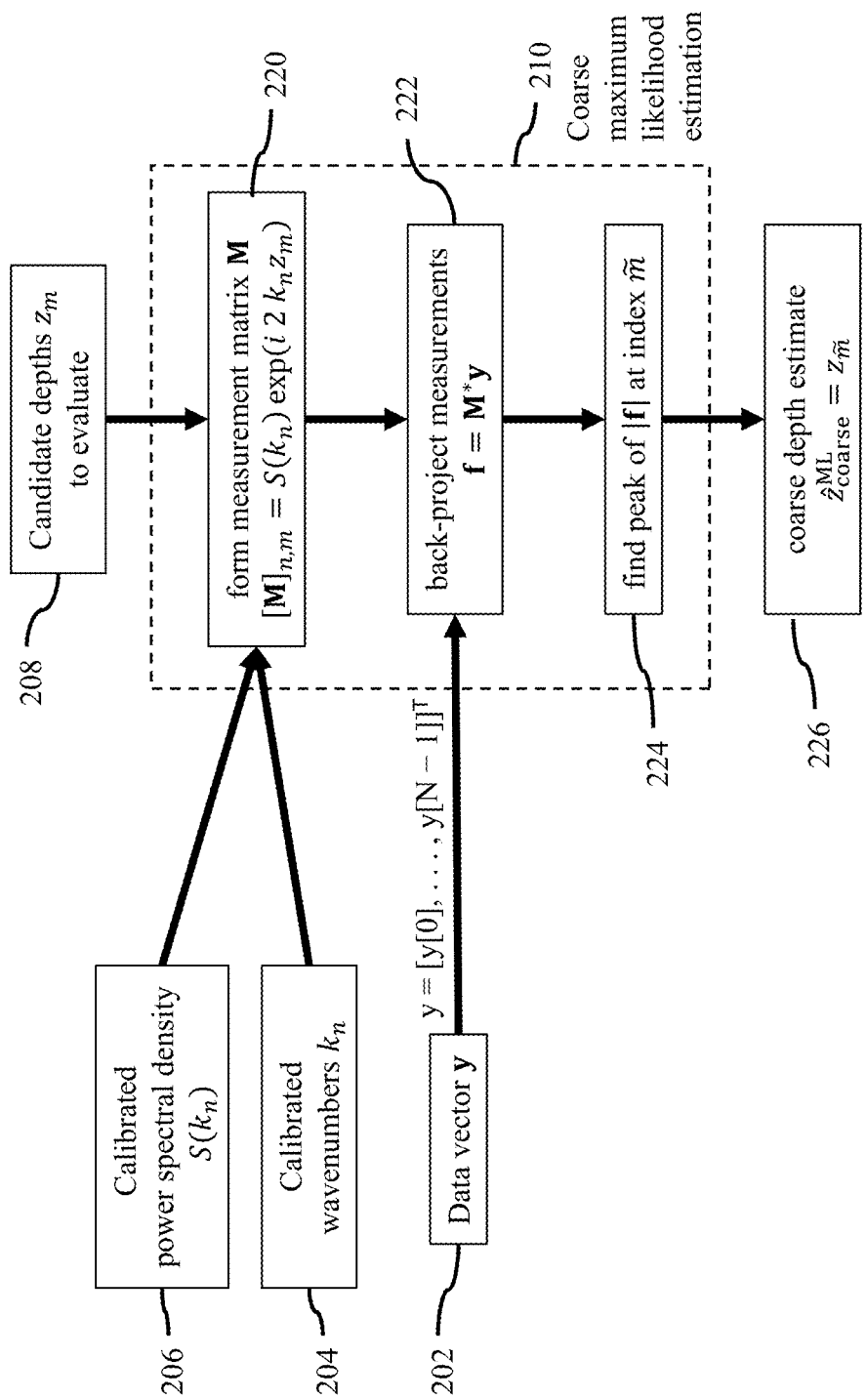
FIG. 2B illustrates the process of determining the maximum likelihood estimator (MLE) for the depth of the specimen surface via backprojection, according to some example embodiments.

FIG. 2B depicts a detailed process leading to the coarse estimation step 210 of FIG. 2A, according to some example embodiments. For the coarse step, some embodiments recognize that a slowly varying PSD leads to the MLE being approximated by the value of z that maximizes $$G(z) = \frac{2}{Q} \left| \sum_{n=0}^{N-1} y_n S(k_n) \exp(-i2k_n z) \right|^2.$$

The advantage of this approximation is that it can be evaluated efficiently at a discrete set of candidate depths via matrix-vector multiplication.

Figure 2C:
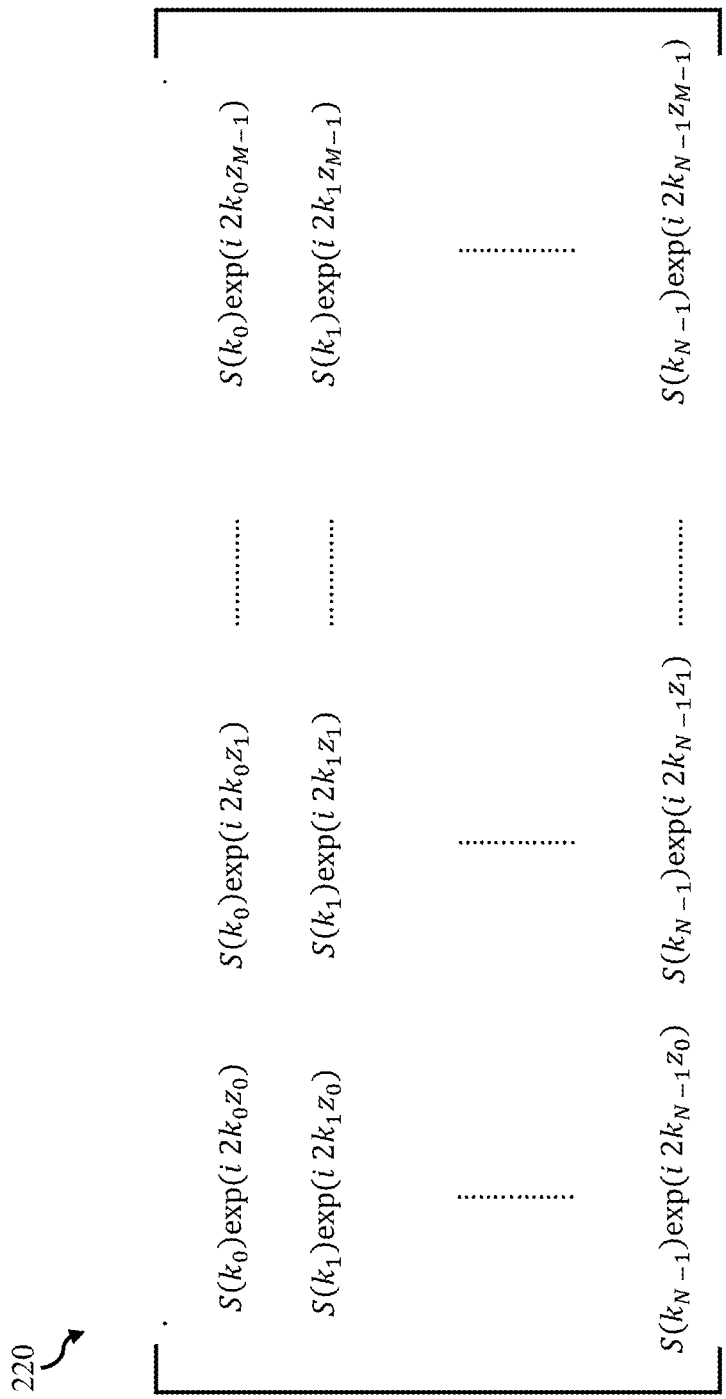
FIG. 2C illustrates one exemplar structure of a measurement matrix utilized for determining the maximum likelihood estimator (MLE) for the depth of the specimen surface, according to some example embodiments.

The discrete measurement matrix M 220 is formed such that the (n, m)th element of the matrix is given as $$[M]_{n,m} = S(k_n) \exp(i2k_n z_m),$$

including the calibrated PSD $S(k_n)$ 206, calibrated wavenumbers $k_n$ 204, and a set of candidate depths $z_m$, (where m=0, ..., M−1) 208. FIG. 2C illustrates one exemplar structure of the measurement matrix M 220, according to some example embodiments. It may be contemplated that any matrix satisfying the aforementioned conditions on its elements may be chosen as the measurement matrix M 220.

Returning back to FIG. 2B, in order to perform the coarse maximum likelihood estimation 210, the data vector 202 is back-projected by the processor through measurement matrix 220 to yield f=M*y, where the * operator denotes the complex conjugate transpose. The magnitude of the back-projection |f| is maximized at index $\tilde{m}$ 224, and the coarse estimate 226 is the corresponding candidate depth $\hat{z}_{coarse}^{ML} = z_{\tilde{m}}$. In many cases, the approximate, coarse estimate is sufficiently accurate. However, it is the recognition of some embodiments that if the measurement has sufficiently high signal-to-noise ratio (SNR), further accuracy can be achieved by maximizing F(z) directly.

Figure 2D:
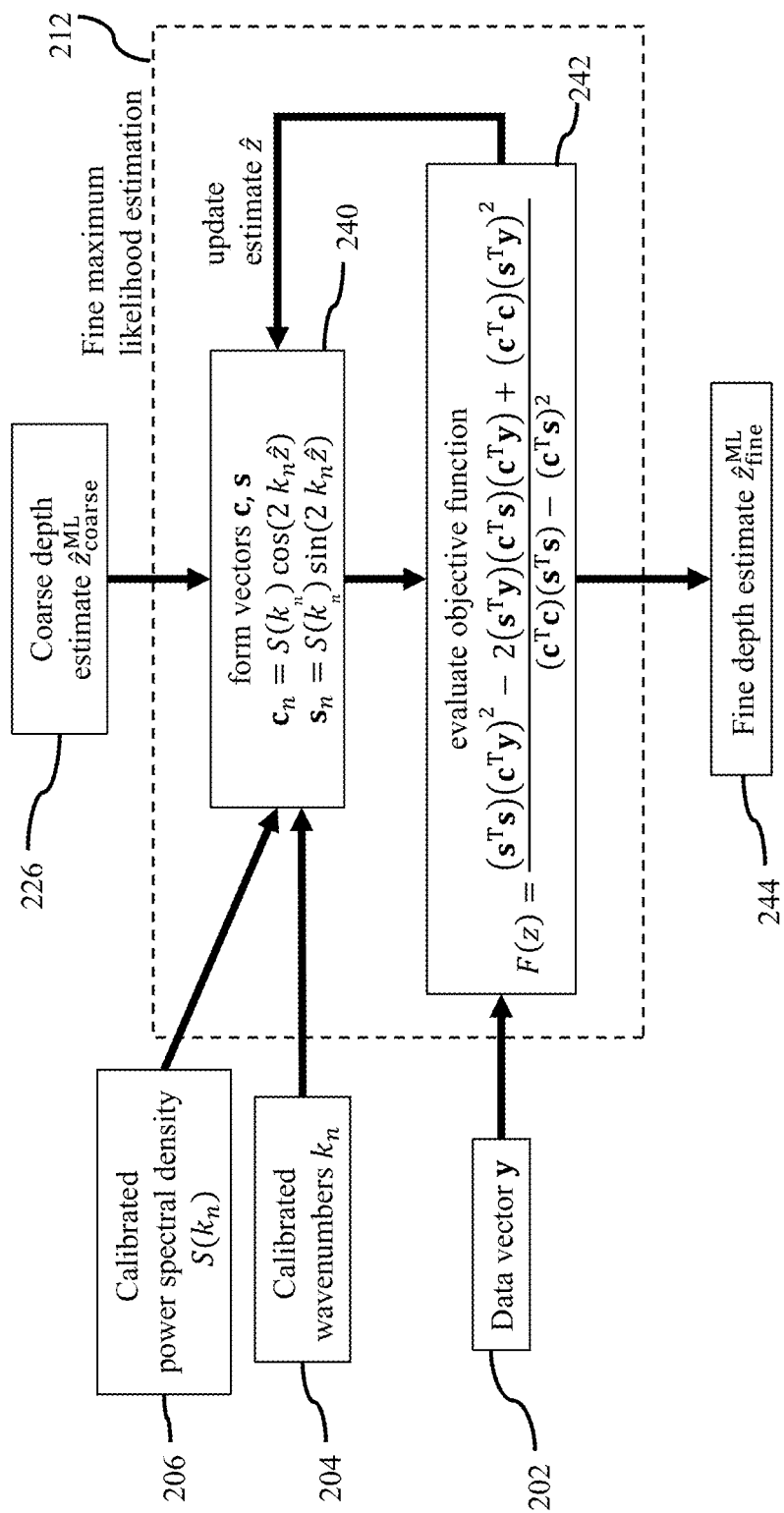
FIG. 2D illustrates the process of determining the maximum likelihood estimator (MLE) for the depth of the specimen surface via refinement of the backprojection estimate, according to some example embodiments.

FIG. 2D depicts the process 212 of refining the coarse MLE. For a given depth z, the cosine and sine column vectors c and s 240 are defined to have the $n^{th}$ element $c_n = S(k_n) \cos(2 k_n z)$ and $s_n = S(k_n) \sin(2 k_n z)$. Then the objective function 242 may be computed as $$F(z) = \frac{(s^T s)(c^T y)^2 - 2(s^T y)(c^T s)(c^T y) + (c^T c)(s^T y)^2}{(c^T c)(s^T s) - (c^T s)^2}.$$

The exact depth MLE, which minimizes the negative log-likelihood, is the value of z for which F(z) is maximized, i.e., $$\hat{z}^{ML} = \arg\max_z F(z).$$

Note that a slowly varying PSD leads to the approximations $c^T s = s^T c \approx 0$ and $c^T c \approx s^T s \approx Q/2$, where $Q = \sum_{n=0}^{N-1} S^2(k_n)$, so $F(z) \approx G(z)$, and the coarse estimate is typically close to the true depth value. Thus, $\hat{z}_{coarse}^{ML}$ is a good initial estimate, which can be further refined by maximizing the exact objective function F(z) using a gradient-free optimization method such as Brent's minimization method or golden section search to produce a refined, continuous-valued estimate 244

$$\hat{z}_{fine}^{ML} = \arg\max_z F(z).$$

According to some example embodiments, the processor 110 of FIGS. 1B and 1C may estimate each profilometry measurement by executing a maximum likelihood estimator (MLE) to produce an argument of the maximum likelihood estimate of the non-zero element in the reflectivity vector corresponding. Each argument of the reflectivity vector corresponds to one of the depth values in the measurement model. The MLE may be an approximate MLE or an exact MLE. In some example embodiments where the MLE is an approximate MLE, the execution of the approximate MLE comprises back-projecting the data vector through the measurement matrix, and the MLE is the depth value corresponding to the largest-magnitude element in the back-projection. In some example embodiments where the MLE is an exact MLE, the execution of the exact MLE comprises refining the approximate MLE by maximizing the maximum likelihood objective function using a gradient-free optimization method such as Brent's minimization method or golden section search.

Advantages of ML Depth Estimation

The common approach for OCT-based surface estimation is to compute the Fourier transform of the data and find the peak. However, the fast Fourier transform (FFT) algorithm cannot be directly applied to the data vector y because the FFT requires that samples of y be uniformly spaced in wavenumber. In a Spectral Domain OCT (SDOCT) system, the dispersive element such as diffraction grating 140 causes an approximately linear change in angle as a function of wavelength. As a result, with reference to FIG. 3, the detector array 142 samples the interference signal uniformly in wavelength 300, leading to nonuniform samples in wavenumber 304.

Figure 3:
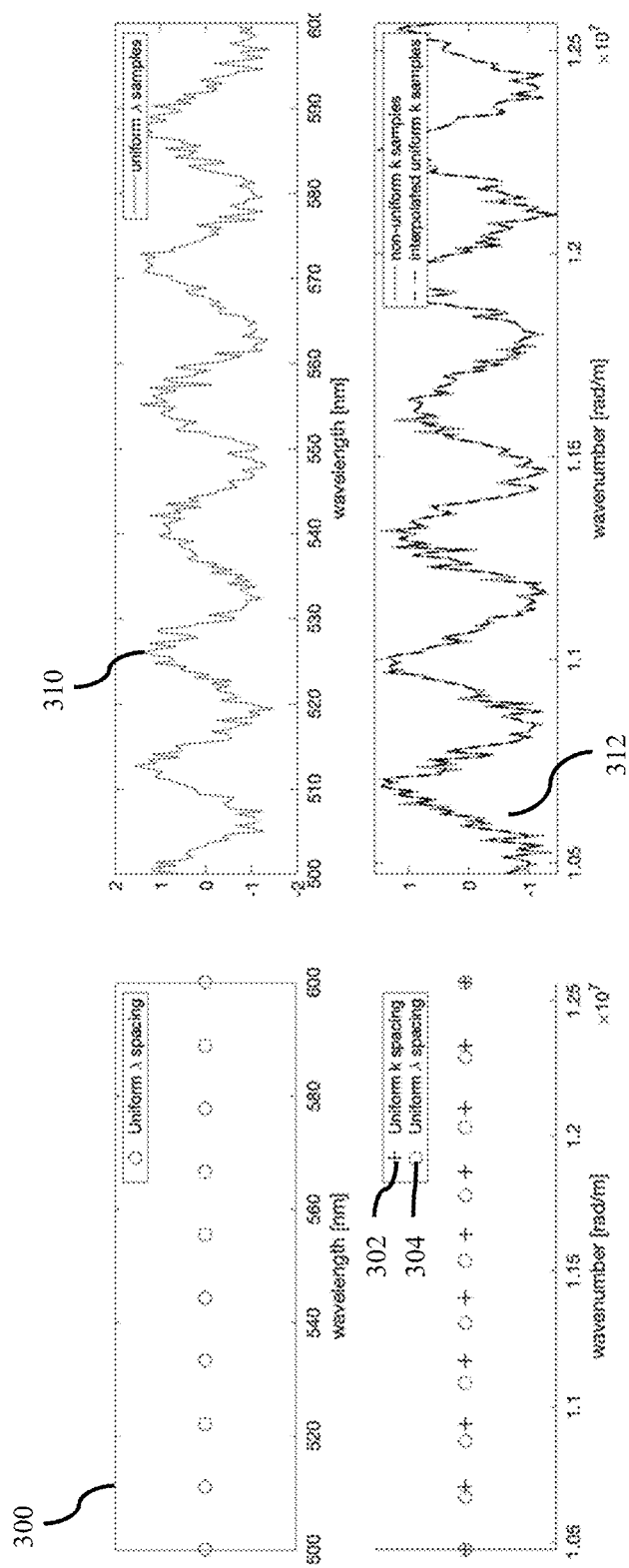
FIG. 3 shows an example scenario depicting sampling of the interference signal leading to samples that are non-uniformly spaced in wavenumber, according to some example embodiments.

In a Swept Source OCT (SSOCT) system, existing methods to achieve samples that are uniform in wavenumber require additional complex hardware. These include determining a nonlinear sweep of the drive current that will produce time samples that are uniform in time or using an arbitrary drive current and an additional reference (e.g., a k-clock based on an etalon or Michelson interferometer) to determine when to sample non-uniformly in time corresponding to uniform wavenumber samples. Instead of employing these complicated methods, uniform wavenumber spacing is typically achieved via software post-processing. The measurement is made at nonuniform wavenumber samples, and the signal is interpolated and resampled so that the sample spacing is uniform in wavenumber 302 (i.e., uniform k spacing) as is shown in FIG. 3.

A second approach for OCT-based surface estimation attempts to invert the measurement y using M and sparse recovery methods, which apply assumptions that the number of surfaces is small. However, the sparse solvers are too general for typical scenarios, which assume that there may be a single surface, and thus these solvers are much slower than the FFT method.

Compared to the FFT method, the ML method has the following advantages. Firstly, the ML method avoids interpolation: The measurement matrix M is defined explicitly at the measured wavenumbers $k_n$, regardless of the distribution of the samples. On the other hand, the fast Fourier transform (FFT) requires measurements to be sampled uniformly in wavenumber. FIG. 3 shows how samples that are uniform in wavelength 300 leads to samples that are nonuniform in wavenumber 304. The measurements made at nonuniform wavenumber 310 must be interpolated and resampled at uniform wavenumber 312 before the FFT can be applied, and interpolation is undesirable because it also interpolates noise.

Figure 4:
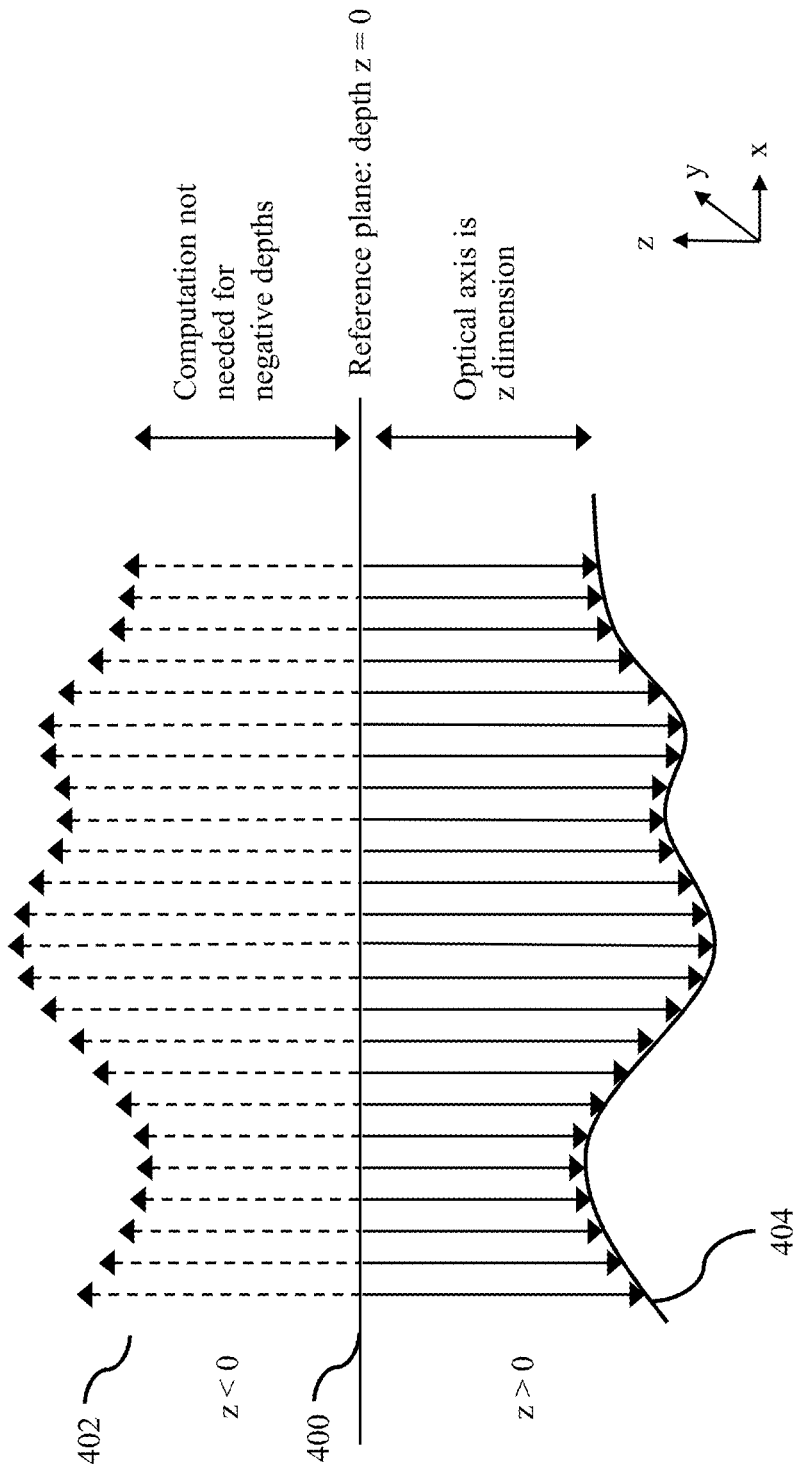
FIG. 4 shows an example scenario depicting how placing a specimen on one side of the reference plane makes it unnecessary to compute both positive and negative depths, according to some example embodiments.

Secondly, the ML method specifies the useful measurement range: Measurement matrix M is defined explicitly for a set of possible depths $z_m$ for m=0, ..., M−1. These $z_m$ can be chosen at whatever coarse or fine resolution is desired and over whatever range of depths is relevant. For instance, OCT measurements typically measure with respect to a reference depth z=0. According to some example embodiments, as shown in FIG. 4, the specimen surface 404 is kept entirely on one side of the reference plane 400 so that no ambiguity occurs. That is, computation is not required for negative depths 402. Therefore, it is straightforward to reconstruct only positive depth values. On the other hand, the FFT automatically calculates the depth profile for both positive depths and negative depths, which adds unnecessary calculation. Furthermore, the FFT resolution is inversely related to the length of the data vector. For finer depth resolution, the measurement is usually padded with zeros to increase its length, which also increases computation time.

Thirdly, the ML method includes all available information: The measurement matrix includes not only the depths and the wavenumbers, but also the power spectral density (PSD) $S(k_n)$. This is equivalent to an amplitude envelope that multiplies the measurements. Including the PSD in M properly accounts for the weight each element of the data should receive in back-projection. The FFT does not include the PSD. As a result, the depth domain is convolved with the Fourier transform of the PSD, and the peak is broadened, making it more difficult to identify the true peak.

Compared to the sparse recovery approach, ML estimation has the additional benefit that the ML method has a fast implementation: Back-projection multiplies the data by the measurement matrix adjoint M* which is trivial to compute (transpose and conjugation). More general sparse reconstruction methods require regularized least-squares solutions, which are iterative and much slower.

Modifications for an SS-OCT System

In an SS-OCT configuration, the illumination source sweeps through one wavelength at a time. The wavelengths are separated in time, so the spectrometer is a single-pixel detector that measures the intensity of the combined light at time samples n=0, ..., N−1 covering the wavelength sweep of the source. Some implementations remove the DC components of the measurement in hardware using a balanced detector.

Calibration Procedure

Figure 5:
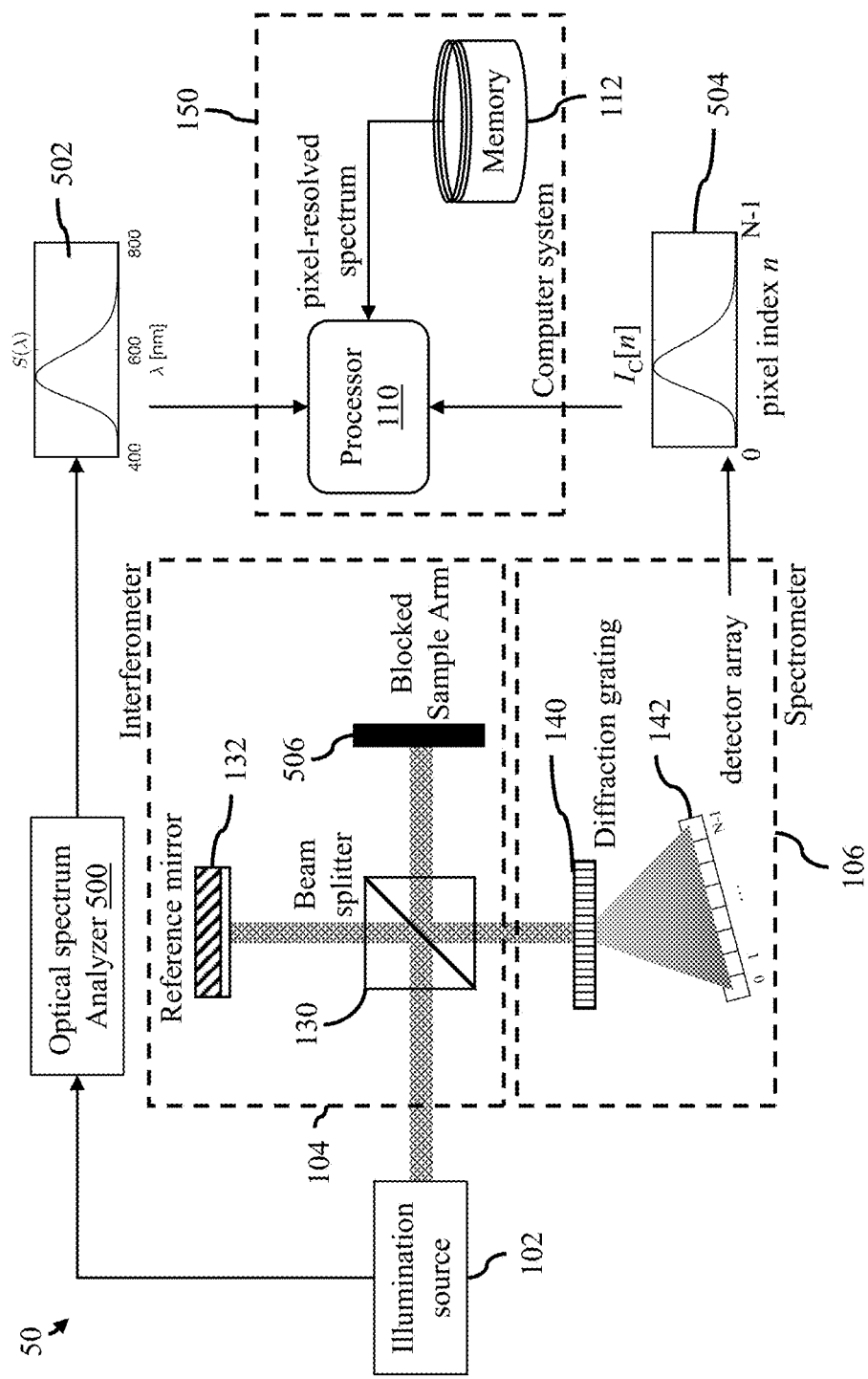
FIG. 5 illustrates a wavelength calibration schematic using an additional optical spectrum analyzer for determining the wavelength associated with each detector pixel of a detector array, according to some example embodiments.

The measurements made by the detector array 142 may be given as $I_D[n]$, however, the data required for estimation may require the transformation of the measurements to the form given by expression 4(a). The detector measurements have linear indices n, but the actual values of $k_n$ are needed to accurately recover the absolute depth. FIG. 5 shows the wavelength calibration schematic for determining the wavelength associated with each detector pixel of the detector array 142, according to some example embodiments. The illumination source 102, the interferometer 104, the spectrometer 106, the computer system 150 may be same as those described with reference to FIG. 1C and operate in a similar manner described in reference thereto. As is shown in FIG. 5, in some example embodiments, a 'reference-only' measurement 504 is made at the detector array 142 by blocking the sample arm 506. For example, the specimen/sample may be masked by a non-reflecting surface to block the sample arm. In this case, the intensity at the detector 142 is only due to the reference arm reflected from the reference mirror 132, so that it includes the power spectral density but none of the interference terms. In some embodiments, the spectrometer 106 has a diffraction grating 140 that causes linear dispersion as a function of wavelength. In such a scenario, the only light reaching the detector array 142 is due to the reference arm. Then the intensity at the detector is:

$$I_C[n] = \frac{1}{2}\langle|E_R|^2\rangle = \frac{\rho}{4}S(k_n)r_R^2. \quad (14)$$

According to some example embodiments, the OCT system 100B may additionally comprise a PSD calibrator for blocking the sample arm of the interferometer 104 so the measurement includes light only from the reference beam propagating in the reference arm of the interferometer 104, such that the measured intensities of the interference pattern are a function of the PSD of the incident light for corresponding wavenumbers scaled with a responsivity of the spectrometer 106 and reflectivity of the reference arm. During execution of the PSD calibrator, the processor 110 is configured to calibrate the PSD of the incident light such that the wavenumber corresponding to each pixel of the spectrometer 106 is estimated.

The reference measurement has indices n, and the associated wavenumber values $k_n$ are unknown. These associated wavenumber values are needed to accurately recover the absolute depth. A method to determine the associated wavenumber values is based on a wavelength calibration procedure which is described next.

The wavenumber calibration procedure is depicted in FIGS. 6A-6E and involves aligning two measurements of the PSD: one made with standard test equipment and one made with the OCT system 50. The source spectrum is measured with an optical spectrum analyzer (OSA) 500, which measures the illumination intensity $I_{GT}(\lambda)$ as a function of wavelength. The $I_{GT}(\lambda)$ is then rescaled and aligned to the reference measurement $I_C[n]$ to find a fit between the measurements that allows mapping pixel indices directly to wavelengths.

Next a ground truth measurement of the illumination source spectrum is made with the optical spectrum analyzer (OSA) 500, which is modeled as $I_{GT}[\ell]=\gamma S(\lambda_l)$, $\ell=1, \ldots, L$. The wavelengths $\lambda_l$ are known but may be sampled non-uniformly and at different locations than $\lambda_n=2\pi/k_n$, and $\gamma$ accounts for any difference in scaling between the instruments. To map the detector index to the true wavelength, the ground truth is aligned with the calibration. Towards this end, the ground truth is interpolated and resampled so that it lies on the same uniform grid as $I_C[n]$. The spacing of the resampling grid is set to ensure that $S(k)$ has the same bandwidth (FWHM or 1/e) in both measurements. Next, $I_{GT}[n]$ and $I_C[n]$ are cross-correlated to find the shift that maximizes the overlap between the spectrum measurements. Using the resampled $\lambda_l$, the detector indices n may be associated with their true wavelengths.

Figure 6A:
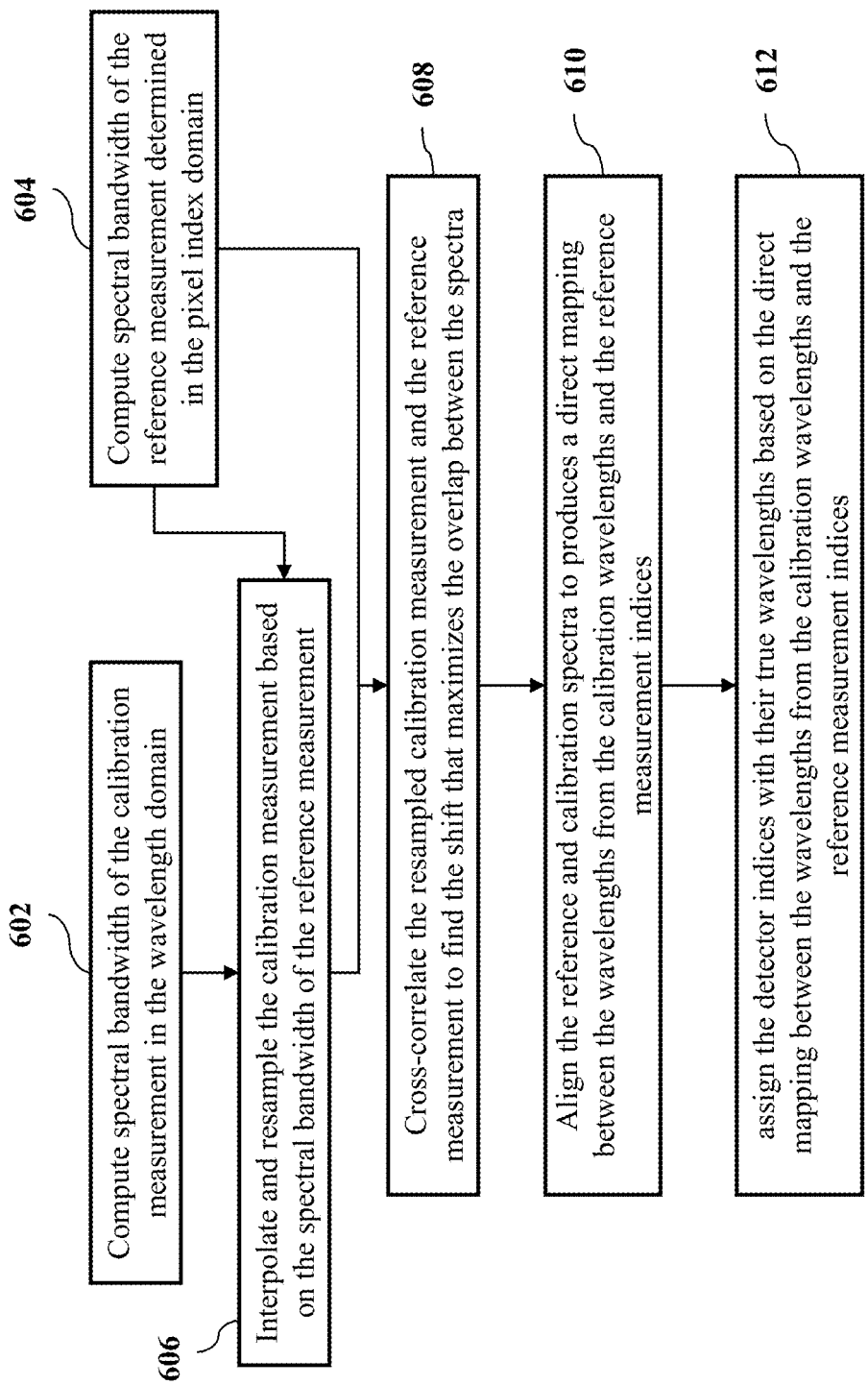
FIG. 6A illustrates a wavenumber calibration method, according to some example embodiments.
Figure 6B:
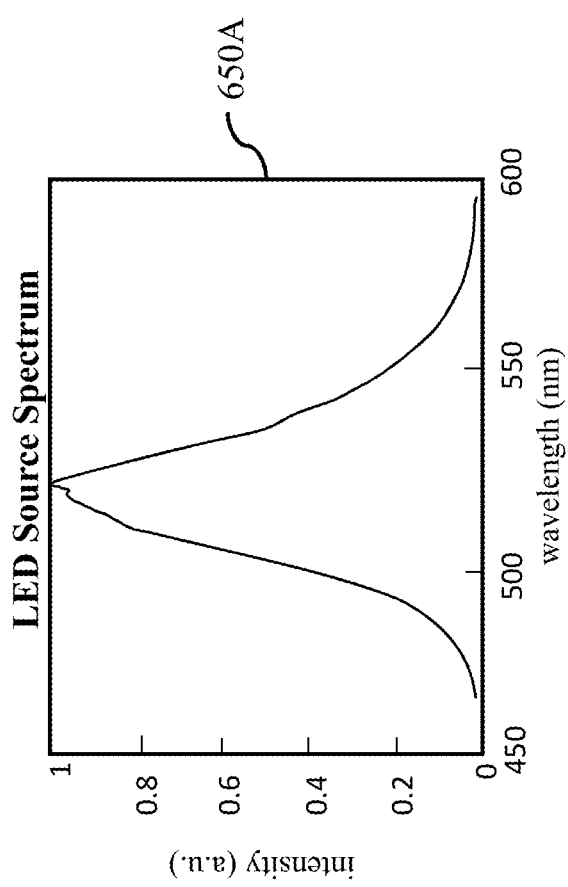
FIG. 6B illustrates an LED source spectrum as the spectral bandwidth of the calibration measurement, according to some example embodiments.
Figure 6C:
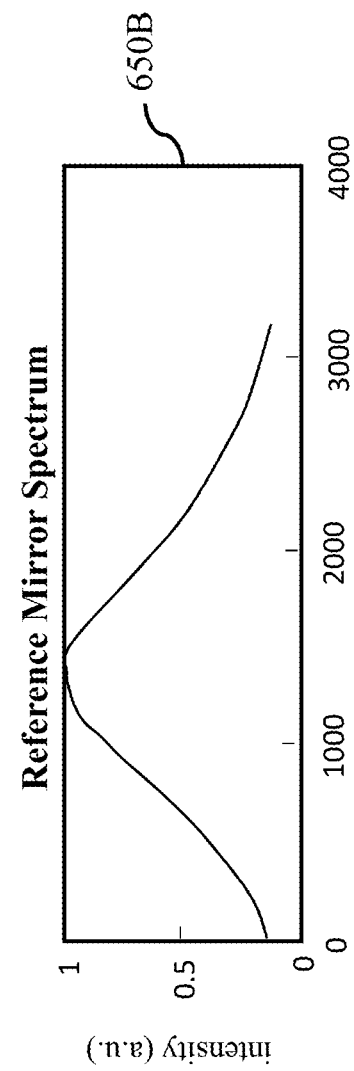
FIG. 6C illustrates a Reference Mirror Spectrum as the spectral bandwidth of the reference measurement, according to some example embodiments.

FIG. 6A illustrates the wavenumber calibration method, according to some example embodiments. FIG. 6A will be described in conjunction with FIG. 5. The optical spectrum analyzer 500 of FIG. 5 provides the calibration measurement 502 while the detector array 142 provides the reference measurement 504 in the manner described above. A processor may compute 602 the spectral bandwidth of the calibration measurement 502 to be BW A c in the wavelength domain (nanometers). The processor may also compute 604 the spectral bandwidth of the reference measurement 504 to be BK R determined in the pixel index domain. Either of the bandwidths may be defined as the full width at half-maximum (FWHM) or 1/e bandwidth or any other suitable definition. FIG. 6B illustrates an LED source spectrum 650A as the spectral bandwidth of the calibration measurement 502 according to some example embodiments. FIG. 6C illustrates a Reference Mirror Spectrum 650B as the spectral bandwidth of the reference measurement 504 according to some example embodiments.

Figure 6D:
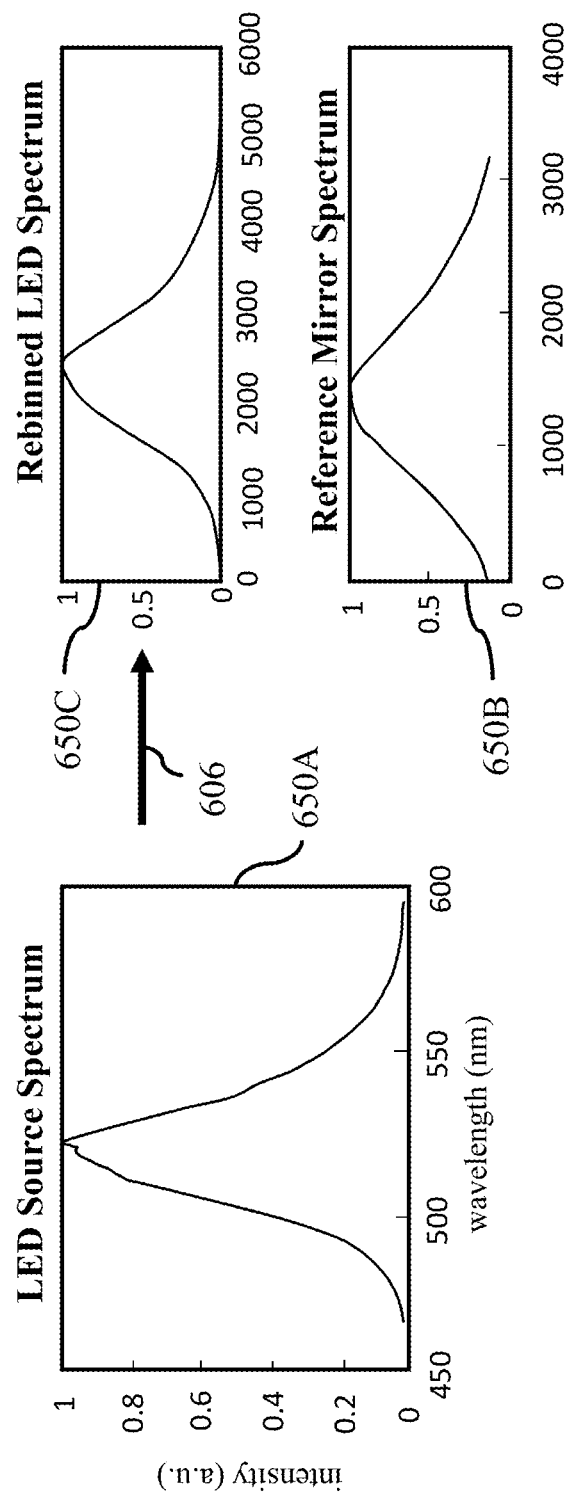
FIG. 6D illustrates interpolation and resampling of the LED source spectrum of FIG. 6B for the wavelength calibration method by spectrum alignment of FIG. 6A, according to some example embodiments.

Referring back to FIG. 6A, the calibration measurement is interpolated and resampled 606 based on the spectral bandwidth of the reference measurement. Particularly, as illustrated in FIG. 6D, the LED source spectrum 650A is interpolated and resampled so that the uniform wavelength sample spacing $\Delta_\lambda = BW_\lambda^C/BW_n^R$ sets the spectral bandwidths 650C and 650B to be equal in numbers of pixel indices.

Figure 6E:
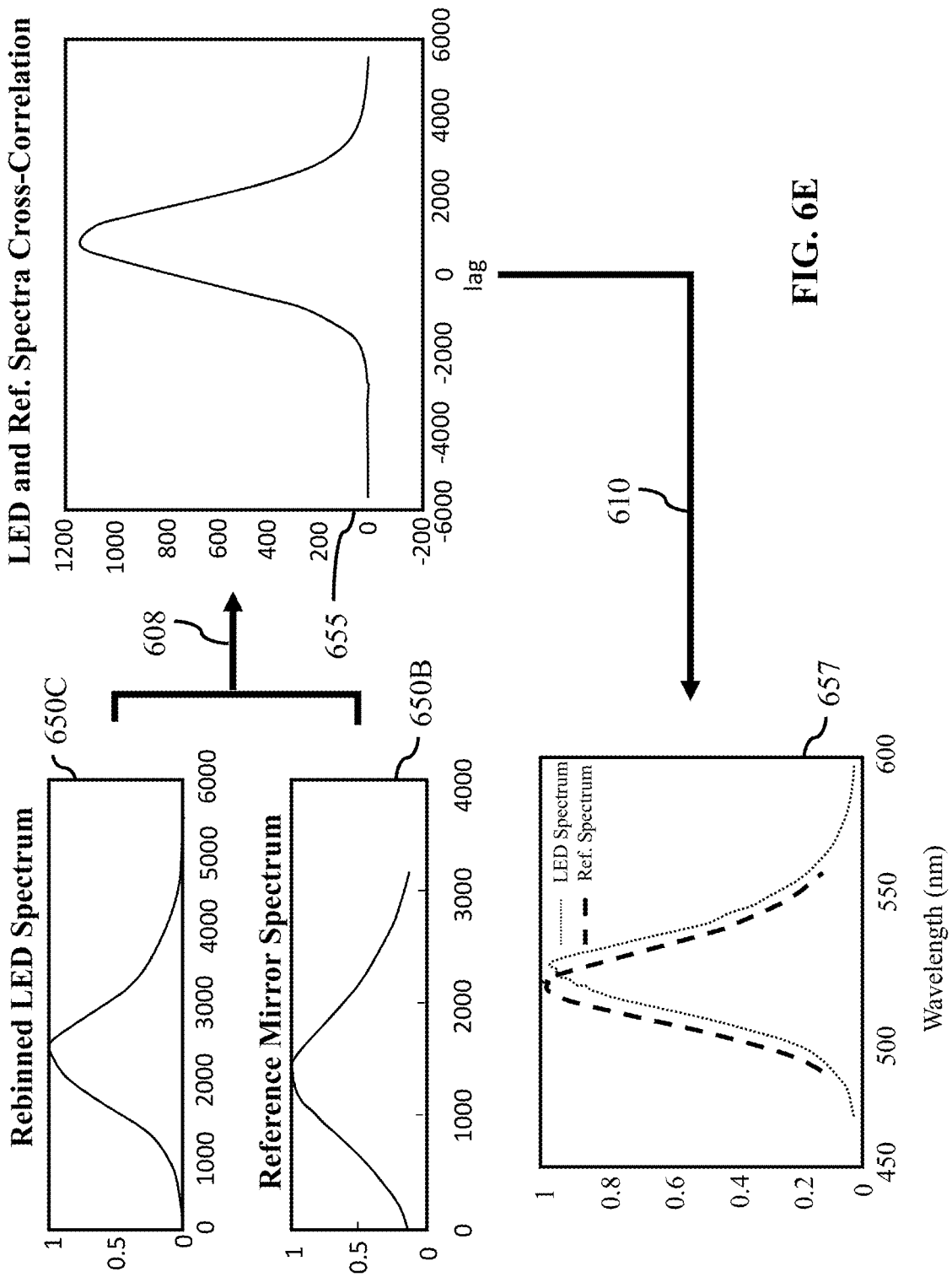
FIG. 6E illustrates the cross correlation between the LED spectrum and the reference mirror spectrum for the wavelength calibration method by spectrum alignment of FIG. 6A, according to some example embodiments.

The resampled calibration measurement 650C and the reference mirror spectrum (i.e., the reference measurement 650B) are then cross correlated 608 to find the shift that maximizes the overlap between the spectra 650C and 650B. The cross correlation 655 between the LED spectrum and the reference mirror spectrum is illustrated in FIG. 6E. The wavelength calibration is finally realized by aligning 610 the two spectra 650C and 650B to produce a direct mapping 657 between the wavelengths from the calibration wavelengths and the reference measurement indices, which is used to assign 612 the detector indices with their true wavelengths.

Figure 7:
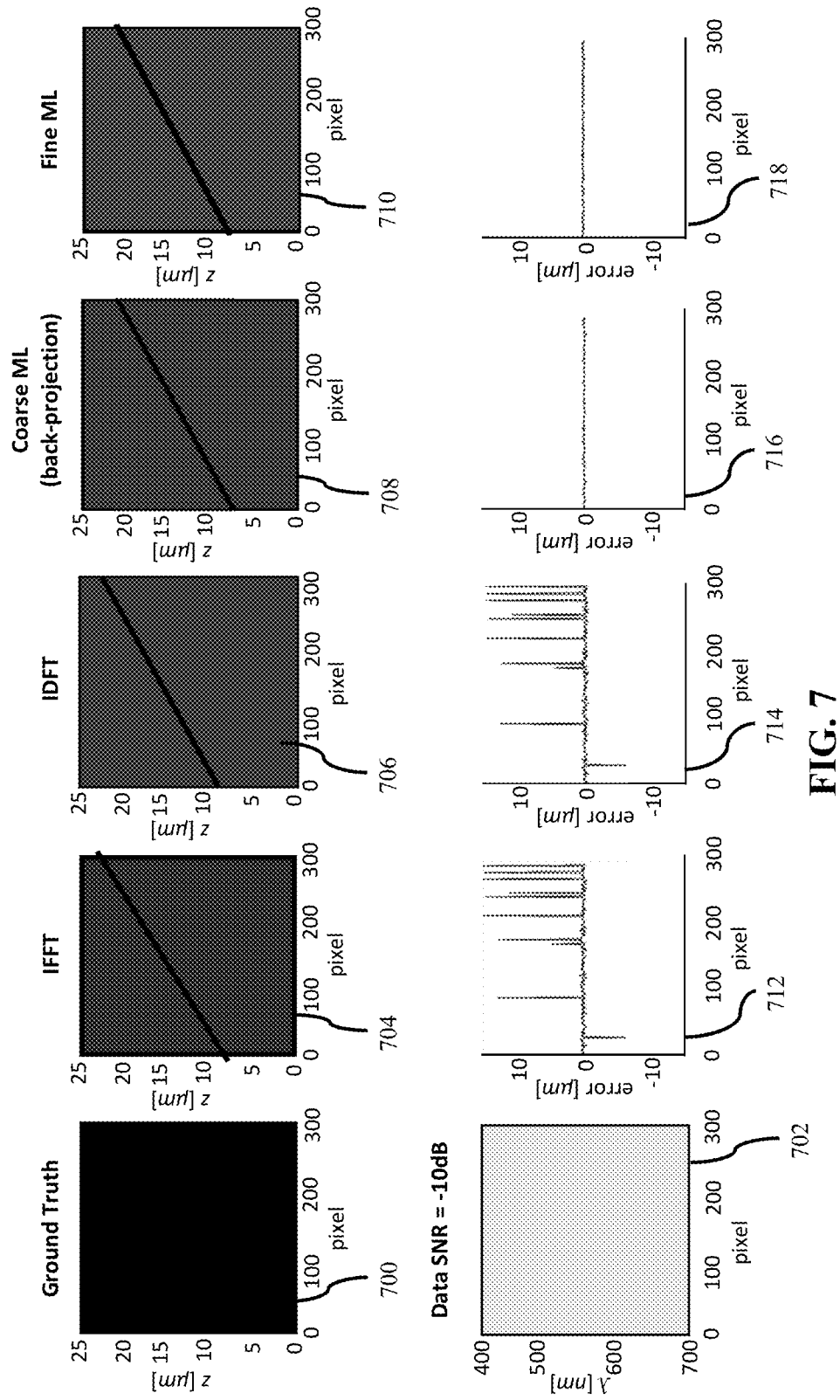
FIG. 7 shows a schematic comparison of experimental results of applying a Maximum Likelihood Estimator to simulated data of OCT surface measurements, according to some example embodiments.

FIG. 7 shows a schematic comparison of experimental results of applying the Maximum Likelihood Estimator to simulated data of OCT surface measurements. It is to be noted that the comparison shown in FIG. 7 is non-limiting and only for illustrative purposes and it is contemplated that the experimental values of various parameters may be configurable to different set of values. The illumination source may be set to have a Gaussian spectrum with center wavelength around 550 nm and FWHM bandwidth of 100 nm. The sample shown in 700 is a 1-dimensional linear ramp spanning depths from roughly 10-23 μm. The reflectivity at each pixel may be set to a constant value of 0.05, and a phase shift is added uniformly at random over [0, 2π). Measurements 702 made at 500 wavelengths, and reconstructions are computed for a 25-nm depth resolution and 25-μm maximum depth. Additive white Gaussian noise is added so the measurements have a −10-dB signal-to-noise-ratio (SNR).

In 704, the conventional approach (IFFT) is applied, using linear interpolation of the measurements 702 to get uniform wavenumber samples, and inverting via the FFT algorithm. The error between the FFT estimate 704 and the ground truth 700 is 712, which shows significant errors in surface depth estimation. In 706, another conventional approach (IDFT) is applied, using linear interpolation of the measurements 702 to get uniform wavenumber samples, but inversion is instead performed by explicitly specifying the partial inverse Discrete Fourier Transform matrix for a small range of only positive depth values. The error between the FFT estimate 706 and the ground truth 700 is 714, which is identical to 712 and shows significant errors in surface depth estimation.

In 708, the coarse step (backprojection) of the proposed maximum likelihood estimator (ML-grid: the depth MLE on a discrete grid) is applied directly to the measurements 702 without interpolation. The surface estimation error between the coarse ML estimate 708 and the ground truth 700 is 716, which is significantly less than 712 and 714. In 710, the fine step of ML estimation (ML-iter: the depth MLE with iterative refinement) is applied directly to the measurements 702 using the result from the coarse step 708 as initialization. The error between the fine ML estimate 710 and the ground truth 700 is 718, which is significantly less than 712. Therefore, example embodiments based on the fine ML estimation approach lead to several advantages over the conventional and available solutions.

Figure 8:
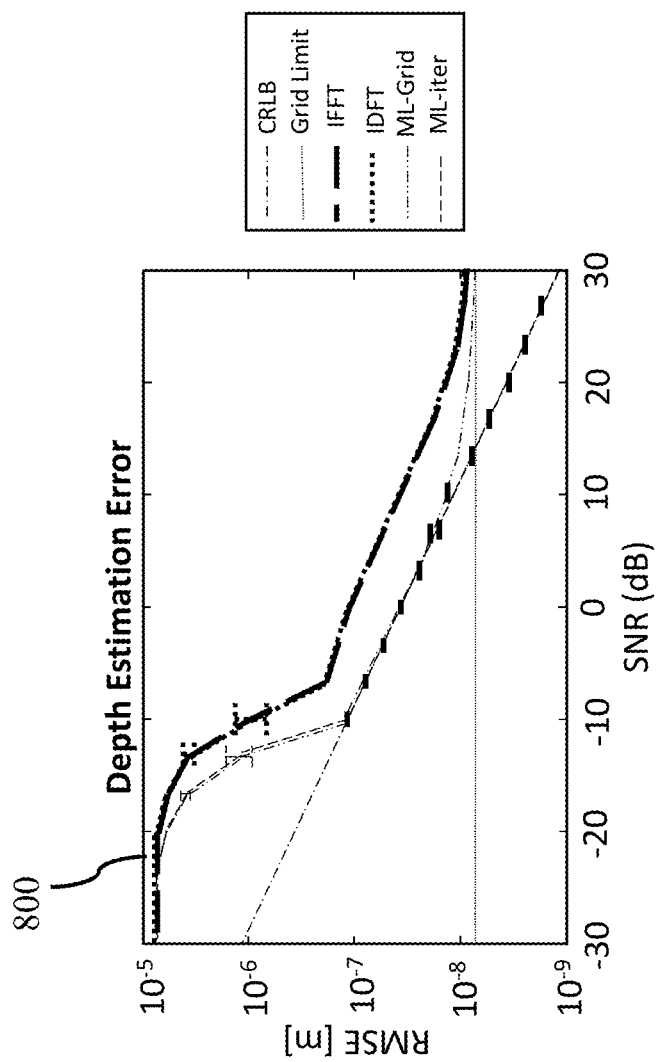
FIG. 8 illustrates a performance comparison between some surface depth estimation methods, according to some example embodiments.

FIG. 8 illustrates a performance comparison between surface depth estimation methods. It is to be noted that the comparison shown in FIG. 7 is non-limiting and only for illustrative purposes and it is contemplated that the experimental values of various parameters may be configurable to different set of values. In 800, the depth estimation root-mean-square error (RMSE) is plotted against the SNR averaged over 10 trials. The RMSE is compared to the square root of the Cramer-Rao lower bound (CRLB), which gives a lower bound on the range accuracy for unbiased estimators. Also plotted is the expected RMSE limit for the discrete estimators. Since the back-projection, FFT, and DFT methods are confined to a discrete grid with grid spacing $\delta_z$, the root mean squared error (RMSE) is limited to $\sqrt{\delta_z^2/12}$, assuming uniformly distributed depths. Plot 800 shows that the MLE yields better results than the FFT and DFT methods. In fact, the ML methods achieve roughly the same RMSE at 10-dB lower SNR than the FFT and DFT methods. The coarse and fine ML methods are essentially the same for 0-dB SNR or lower, whereas the iterative refinement improves estimation performance as the SNR increases and achieves the CRLB above −10-dB SNR. Both the ML-grid and Fourier methods are limited by the discretization of the depth grid size at high SNR.

The coarse ML estimator (back-projection) is faster than the inverse DFT matrix because it avoids the wavenumber interpolation step. Both the coarse ML estimator and inverse DFT methods with explicitly defined matrices are faster than the inverse FFT algorithm, which performs unnecessary computation for negative and out-of-range depth values. The fine ML estimator method requires just twice the runtime of the conventional FFT-based approach.

Figure 9:
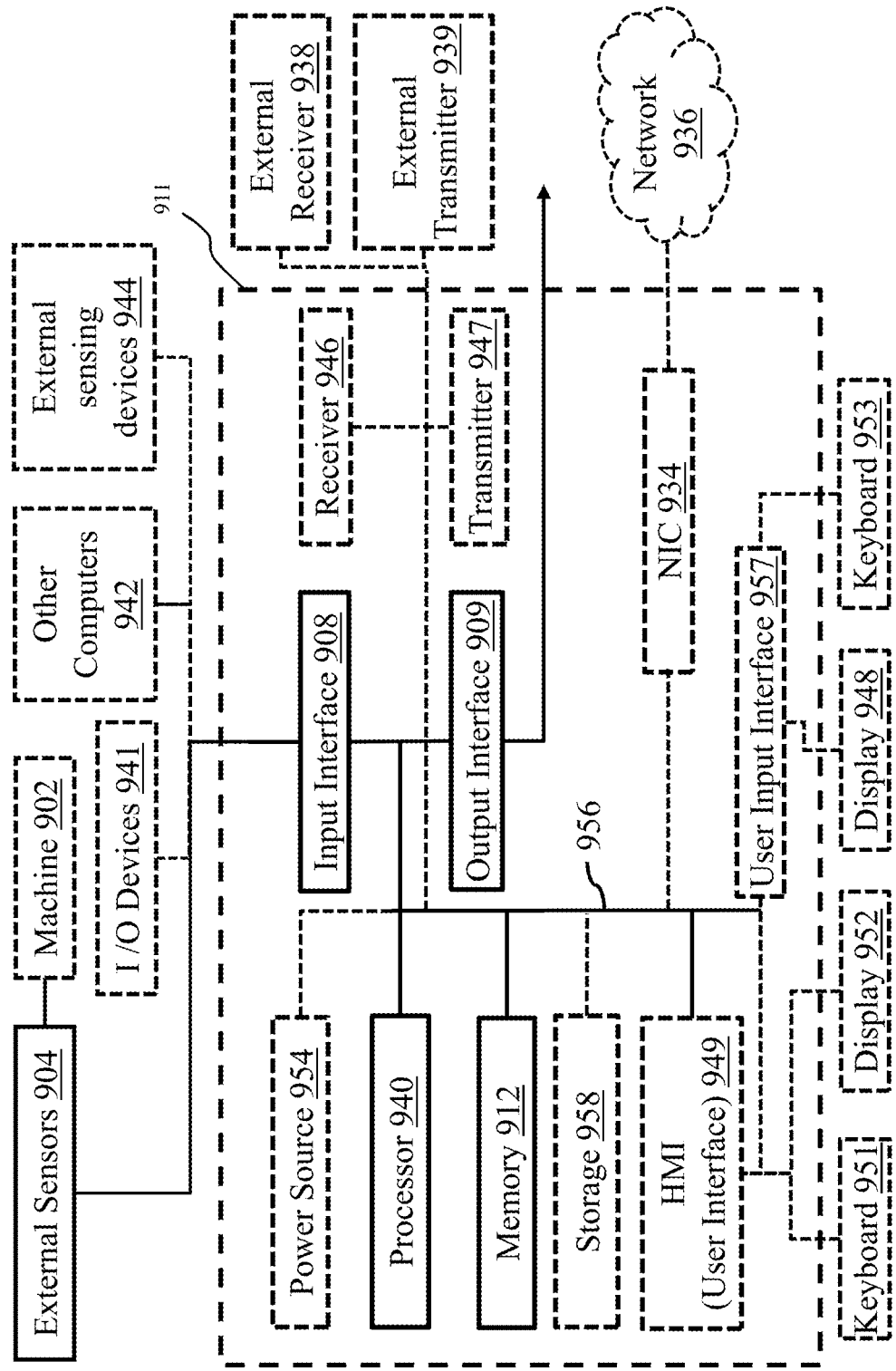
FIG. 9 illustrates a block diagram of a system for implementing OCT, according to some example embodiments.

FIG. 9 illustrates a block diagram of a system for implementing OCT, according to embodiments of the present disclosure. The computer 711 includes a processor 940, computer readable memory 912, storage 958 and user interface 949 with display 952 and keyboard 951, which are connected through bus 956. For example, the user interface 964 in communication with the processor 940 and the computer readable memory 912, acquires and stores the image data in the computer readable memory 912 upon receiving an input from a surface, keyboard 953, of the user interface 957 by a user.

The computer 911 can include a power source 954, depending upon the application the power source 954 may be optionally located outside of the computer 911. Linked through bus 956 can be a user input interface 957 adapted to connect to a display device 948, wherein the display device 948 can include a computer monitor, camera, television, projector, or mobile device, among others. A network interface controller (NIC) 934 is adapted to connect through the bus 956 to a network 936, wherein image data or other data, among other things, can be rendered on a third-party display device, third party imaging device, and/or third-party printing device outside of the computer 911.

Still referring to FIG. 9, the image data or other data, among other things, may be transmitted over a communication channel of the network 936, and/or stored within the storage system 958 for storage and/or further processing. Further, the time series data or other data may be received wirelessly or hard wired from a receiver 946 (or external receiver 938) or transmitted via a transmitter 947 (or external transmitter 939) wirelessly or hard wired, the receiver 946 and transmitter 947 are both connected through the bus 956. The computer 911 may be connected via an input interface 908 to external sensing devices 944 and external input/output devices 941. For example, the external sensing devices 904 may include sensors gathering data before-during-after of the collected time-series data of the machine. The computer 911 may be connected to other external computers 942. An output interface 909 may be used to output the processed data from the processor 940. It is noted that a user interface 949 in communication with the processor 940 and the non-transitory computer readable storage medium 912, acquires and stores the region data in the non-transitory computer readable storage medium 912 upon receiving an input from a surface of the user interface 949 by a user.

The above description provides exemplary embodiments only, and is not intended to limit the scope, applicability, or configuration of the disclosure. Rather, the following description of the exemplary embodiments will provide those skilled in the art with an enabling description for implementing one or more exemplary embodiments. Contemplated are various changes that may be made in the function and arrangement of elements without departing from the spirit and scope of the subject matter disclosed as set forth in the appended claims.

Specific details are given in the following description to provide a thorough understanding of the embodiments. However, understood by one of ordinary skill in the art can be that the embodiments may be practiced without these specific details. For example, systems, processes, and other elements in the subject matter disclosed may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements. Also, individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed but may have additional steps not discussed or included in a figure. Furthermore, not all operations in any particularly described process may occur in all embodiments. A process may correspond to a method, a function, a procedure, a subroutine, a subprogram, etc. When a process corresponds to a function, the function's termination can correspond to a return of the function to the calling function or the main function.

Furthermore, embodiments of the subject matter disclosed may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine-readable medium. A processor(s) may perform the necessary tasks. Various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. Typically, the functionality of the program modules may be combined or distributed as desired in various embodiments.

Embodiments of the present disclosure may be embodied as a method, of which an example has been provided. The acts performed as part of the method may be ordered in any suitable way. Accordingly, embodiments may be constructed in which acts are performed in an order different than illustrated, which may include performing some acts concurrently, even though shown as sequential acts in illustrative embodiments. Further, use of ordinal terms such as "first," "second," in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Although the present disclosure has been described with reference to certain preferred embodiments, it is to be understood that various other adaptations and modifications can be made within the spirit and scope of the present disclosure. Therefore, it is the aspect of the append claims to cover all such variations and modifications as come within the true spirit and scope of the present disclosure.

What is claimed is:

1. An optical coherence tomography (OCT) system for profilometry measurements of a specimen, comprising:
   an interferometer configured to split incident light into a reference beam and a test beam, and to interfere the test beam reflected from the specimen with the reference beam reflected from a reference mirror to produce an interference pattern;
   a spectrometer configured to analyze spectral components of the interference pattern at non-uniformly sampled wavenumbers;
   a computer-readable memory configured to store a measurement model with elements connecting different depth values with different non-uniformly sampled wavenumbers and weighted with weights derived from a power spectral density (PSD) of the incident light for corresponding wavenumbers; and
   a processor configured to determine the profilometry measurements of the specimen as a maximum likelihood estimate of the specimen surface depth by back-projection of measured intensities of the interference pattern with the measurement model.

2. The OCT system of claim 1, wherein the depth values are uniformly sampled from a depth-measurement range with a resolution of the OCT system, and wherein the depth values are relative values with respect to a reference depth selected outside of the depth-measurement range.

3. The OCT system of claim 1, wherein the processor is configured to estimate each profilometry measurement by executing a maximum likelihood estimator (MLE) to produce an argument of the maximum likelihood estimate of a non-zero element in a reflectivity vector corresponding, wherein each argument of the reflectivity vector corresponds to one of the depth values in the measurement model.

4. The OCT system of claim 3, wherein the MLE is an approximate MLE, and wherein the execution of the approximate MLE comprises back-projecting a data vector through a measurement matrix, and the MLE is the depth value corresponding to the largest-magnitude element in the back-projection.

5. The OCT system of claim 3, wherein the MLE is an exact MLE, and wherein the execution of the exact MLE comprises refining an approximate MLE by maximizing the maximum likelihood objective function using a gradient-free optimization method.

6. The OCT system of claim 1, wherein the spectrometer comprises:
   a diffraction grating configured to diffract different beams of different wavelengths forming the interference pattern into different diffraction angles; and
   a detector array with detecting elements arranged at the different diffraction angles to measure intensities of different beams corresponding to the intensities of uniformly sampled wavelengths in the interference pattern.

7. The OCT system of claim 6, wherein the detecting elements of the detector array are calibrated to map each index of the detecting elements in the detector array with a corresponding wavelength.

8. The OCT system of claim 1, wherein the incident light includes an electromagnetic two-dimensional (2D) field directed by the interferometer to form an axial scan of the specimen, such that the measured intensities of the interference pattern include measurements corresponding to a sequence of points on a line of the specimen, wherein the processor is further configured to:
   extract a sequence of intensities corresponding to the sequence of points; and
   process the intensities of different points concurrently with each, to produce the profilometry measurements for the sequence of points.

9. The OCT system of claim 8, further comprising:
   a plurality of processing circuitry including the processor, for producing in parallel, the profilometry measurements for at least some points in the sequence of points.

10. The OCT system of claim 8, further comprising:
    an actuator to direct the incident light into another line parallel to a line of a previous scan.

11. The OCT system of claim 1, further comprising:
    an illumination source for producing the incident light, the illumination source includes one or a combination of a laser, a superluminescent diode (SLD), or a light-emitting diode (LED).

12. The OCT system of claim 1, further comprising:
    a line-field generator including an extended light source of an angular size greater than a lateral resolution across the profilometry measurements, a lens arranged on a path of light emitted by the extended light source for focusing the light into an extended line-field light of a width greater than the lateral resolution, and a filter arranged in a focal plane of the lens for spatially filtering the extended line-field light into the incident light with a line-field of a width equal to the lateral resolution.

13. The OCT system of claim 1, wherein the interferometer is a Michelson interferometer or a Linnik interferometer.

14. The OCT system of claim 1, further comprising:
    a PSD calibrator configured to block a sample arm of the interferometer so the measurement includes light only from the reference beam propagating in a reference arm of the interferometer, such that the measured intensities of the interference pattern are a function of the PSD of the incident light for corresponding wavenumbers scaled with a responsivity of the spectrometer and reflectivity of the reference arm, and wherein during execution of the PSD calibrator, the processor is configured to calibrate the PSD of the incident light such that the wavenumber corresponding to each pixel of the spectrometer is estimated.

15. A method for profilometry measurements of a specimen in an optical coherence tomography (OCT) system, the method comprising:
    splitting by an interferometer, incident light into a reference beam and a test beam, and interfering the test beam reflected from the specimen with the reference beam reflected from a reference mirror to produce an interference pattern;
    analyzing by a spectrometer, spectral components of the interference pattern at non-uniformly sampled wavenumbers;
    wherein a computer-readable memory of the OCT system stores a measurement model with elements connecting different depth values with different non-uniformly sampled wavenumbers and weighted with weights derived from a power spectral density (PSD) of the incident light for corresponding wavenumbers; and determining the profilometry measurements of the specimen as a maximum likelihood estimate of the specimen surface depth by back-projection of measured intensities of the interference pattern with the measurement model.

16. The method of claim 15, wherein the depth values are uniformly sampled from a depth-measurement range with a resolution of the OCT system, and wherein the depth values are relative values with respect to a reference depth selected outside of the depth-measurement range.

17. The method of claim 15, further comprising estimating each profilometry measurement by executing a maximum likelihood estimator (MLE) to produce an argument of the maximum likelihood estimate of a non-zero element in a reflectivity vector corresponding, wherein each argument of the reflectivity vector corresponds to one of the depth values in the measurement model.

18. The method of claim 17, wherein the MLE is an approximate MLE, and wherein the execution of the approximate MLE comprises back-projecting a data vector through a measurement matrix, and the MLE is the depth value corresponding to the largest-magnitude element in the back-projection.

19. The method of claim 17, wherein the MLE is an exact MLE, and wherein the execution of the exact MLE comprises refining an approximate MLE by maximizing the maximum likelihood objective function using a gradient-free optimization method.

20. A non-transitory computer readable medium having stored thereon computer-executable instructions which when executed by a computer, causes the computer to perform a method for profilometry measurements of a specimen in an optical coherence tomography (OCT) system, the method comprising:

splitting by an interferometer, incident light into a reference beam and a test beam, and interfering the test beam reflected from the specimen with the reference beam reflected from a reference mirror to produce an interference pattern;

analyzing by a spectrometer, spectral components of the interference pattern at non-uniformly sampled wavenumbers;

wherein a computer-readable memory of the OCT system stores a measurement model with elements connecting different depth values with different non-uniformly sampled wavenumbers and weighted with weights derived from a power spectral density (PSD) of the incident light for corresponding wavenumbers; and determining the profilometry measurements of the specimen as a maximum likelihood estimate of the specimen surface depth by back-projection of measured intensities of the interference pattern with the measurement model.

* * * * *